United States Patent [19]

Itoh et al.

[11] Patent Number: 5,677,464

[45] Date of Patent: Oct. 14, 1997

[54] PRODUCTION OF OPTICALLY ACTIVE TRIAZOLE COMPOUNDS AND THEIR INTERMEDIATES

[75] Inventors: Katsumi Itoh; Akihiro Tasaka; Hiroshi Hosono, all of Osaka, Japan

[73] Assignee: Takeda Chemical Industries, Ltd., Osaka, Japan

[21] Appl. No.: 453,968

[22] Filed: May 30, 1995

[30] Foreign Application Priority Data

May 31, 1994 [JP] Japan ................................. 6-119147
Jan. 20, 1995 [JP] Japan ................................. 7-007576

[51] Int. Cl.⁶ ............................................. C07D 233/70
[52] U.S. Cl. .................. 548/264.6; 548/110; 548/251; 548/323.5
[58] Field of Search ................. 548/110, 264.6, 548/323.5

[56] References Cited

U.S. PATENT DOCUMENTS 5,371,101  12/1994  Itoh ............................. 514/383

FOREIGN PATENT DOCUMENTS

| 2132791 | 3/1995 | Canada. |
| 0 421 210 | 9/1990 | European Pat. Off.. |
| 0 506 341 | 3/1992 | European Pat. Off.. |
| 0 548 553 | 11/1992 | European Pat. Off.. |
| 0 567 982 | 11/1993 | European Pat. Off.. |
| 0 657 449 A1 | 5/1995 | European Pat. Off.. |
| 2 159 148 | 11/1985 | United Kingdom. |
| WO 95/22973 | 8/1995 | WIPO. |

*Primary Examiner*—Robert Gerstl
*Attorney, Agent, or Firm*—Foley & Lardner

[57] ABSTRACT

A compound of the formula (V):

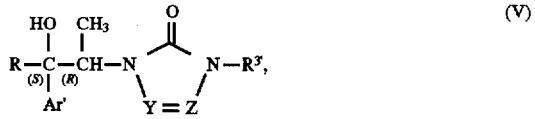

wherein Ar' is a halogenated phenyl group, R is a hydrocarbon residue having a functional group at the α-carbon, $R^{3'}$ is an optionally substituted aliphatic or aromatic hydrocarbon residue or an optionally substituted aromatic heterocyclic group, Y and Z are, the same or different, a nitrogen atom or a methine group optionally substituted with a lower alkyl group, and (R) and (S) represent configurations, which is an optically active intermediate for production of optically active triazole compounds (I):

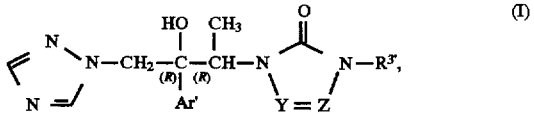

wherein the symbols have the same meanings as defined above, and methods of preparing the compounds (V) and (I).

32 Claims, No Drawings

PRODUCTION OF OPTICALLY ACTIVE TRIAZOLE COMPOUNDS AND THEIR INTERMEDIATES

BACKGROUND OF THE INVENTION

1. Field of the Invention

The present invention relates to a method of preparing optically active triazole compounds useful as a therapeutic agent for fungal infections (antifungal agent), and their intermediates.

2. Description of the Related Art

European Laid Open Patent Publication No. 567982 discloses triazole compounds having an antifungal activity, which are represented by the formula:

wherein Ar is a substituted phenyl group, $R^1$ and $R^2$ are, the same or different, a hydrogen atom or a lower alkyl group or may be combined to form a lower alkylene group, $R^3$ is a group bonded through a carbon atom, $R^4$ is a hydrogen atom or an acyl group, X is a nitrogen atom or a methine group, and Y and Z are, the same or different, a nitrogen atom or a methine group optionally substituted with a lower alkyl group, or a salt thereof.

The above-mentioned publication illustrates as a preferable group of optically active triazole compounds represented by the formula (I):

wherein Ar' is a halogenated phenyl group, $R^{3'}$ is an optionally substituted aliphatic or aromatic hydrocarbon residue or an optionally substituted aromatic heterocyclic group, Y and Z have the same meanings as defined above, and (R) represents a configuration, and further discloses an chiral synthetic method using (R)-lactic acid derivatives as a starting material for a method of preparing the same.

It has been demanded to provide a method of preparing the optically active triazole compounds of the formula (I) and the related compounds, which are useful as a therapeutic agent for fungal infections, in a highly stereoselective and economical manner.

SUMMARY OF THE INVENTION

The present invention provides:

(1) a compound of the formula (V):

wherein Ar' is a halogenated phenyl group, R is a hydrocarbon residue having a functional group at the α-carbon, $R^{3'}$ is an optionally substituted aliphatic or aromatic hydrocarbon residue or an optionally substituted aromatic heterocyclic group, Y and Z are, the same or different, a nitrogen atom or a methine group optionally substituted with a lower alkyl group, and (R) and (S) represent configurations, (2) a method of preparing the compound of the formula (V):

wherein the symbols have the same meanings as defined above, which comprises reacting a compound of the formula (II):

wherein the symbols have the same meanings as defined above, with a Grignard reagent of the formula (XXXI):

$$R-MgX \qquad (XXXI),$$

wherein X is a halogen atom and R has the same meaning as defined above, (3) a method in accordance with the above mentioned method (2), in which a product given by using in the above method (2) a Grignard reagent of the formula (XI):

wherein R', R" and R'" are, the same or different, a lower alkyl group or a lower alkoxy group and $X^2$ is a halogen atom, is oxidized to give a compound of the formula (V'):

wherein the symbols have the same meanings as defined above, and then, the resulting compound of the formula (V') after activating a hydroxyl group upon necessity is reacted with 1H-1,2,4-triazole or a salt thereof to give an optically active triazole compound of the formula (I):

wherein the symbols have the same meanings as defined above, or a salt thereof, (4) a compound of the formula (Va'):

wherein the symbols have the same meanings as defined above, (5) a method of preparing the compound of the formula (Va'):

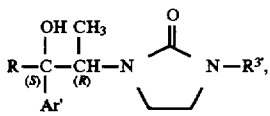 (Va')

wherein the symbols have the same meanings as defined above, which comprises reducing a compound of the formula (Va):

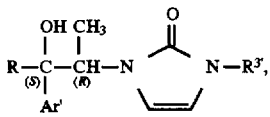 (Va)

wherein the symbols have the same meanings as defined above, (6) a method of preparing the compound of the formula (I'):

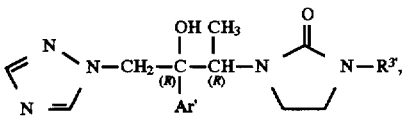 (I')

wherein the symbols have the same meanings as defined above, or a salt thereof, which comprises reacting a compound of the formula (Va"):

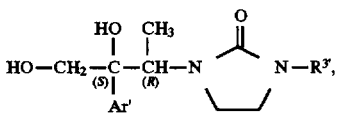 (Va")

wherein the symbols have the same meanings as defined above, with 1H-1,2,4-triazole or a salt thereof, after activating a hydroxyl group of the compound (Va") with an activating agent, (7) an optically active compound of the formula (XIX'):

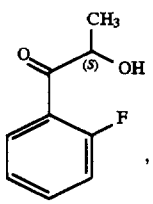 (XIX')

wherein (S) shows that the carbon atom marked with (S) has (S)-configuration, and (8) a method of producing an optically active compound of the formula (XIX'):

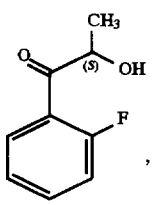 (XIX')

wherein (S) has the same meaning as defined above, which comprises reacting a compound of the formula (XVII):

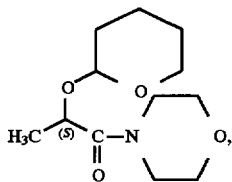 (XVII)

wherein (S) has the same meaning as defined above, with a compound of the formula (XXXII):

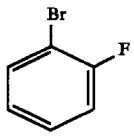 (XXXII)

in presence of magnesium to produce a compound of the formula (XVIII'):

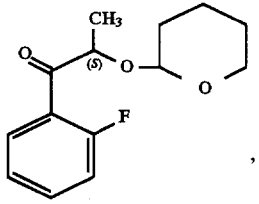 (XVIII')

wherein (S) has the same meaning as defined above, followed by the treatment with a deprotecting agent.

DETAILED DESCRIPTION OF THE INVENTION

The detailed description will be given in the definitions of the formulae (I), (I'), (II), (V), (V'), (Va), (Va'), (Va") (XI), (XII), (XIII) and (XXXI), hereinafter.

Examples of the "halogenated phenyl groups" represented by Ar' include phenyl groups having one to three halogen atoms selected from the group of fluorine, chlorine, bromine and iodine, such as 2,4-difluorophenyl, 2,4-dichlorophenyl, 4-chlorophenyl, 4-fluorophenyl, 2-chlorophenyl, 2-fluorophenyl, 2-fluoro-4-chlorophenyl, 2-chloro-4-fluorophenyl, 2,4,6-trifluorophenyl and 4-bromophenyl, among which phenyl groups substituted with one or two fluorine atoms are preferred.

Examples of the functional groups for the "hydrocarbon residues having a functional group at the α-carbon" represented by R include those which do not impede the reaction, such as a silyl group, a double bond and an optionally activated hydroxyl group.

Examples of the "optionally activated hydroxyl groups" include all of those which may be substituted with 1,2,4-triazol-1-yl group, among which groups represented by $R^5SO_3-$, wherein $R^5$ is a lower alkyl group or an optionally substituted phenyl group, are preferred.

Examples of the "hydrocarbon residues having a functional group at the α-carbon" represented by R are a methine group and a methylene group.

In particular, preferred examples of R are those represented by the formula:

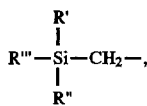

wherein R', R" and R'" are, the same or different, a lower alkyl group or a lower alkoxy group, $H_2C=CH-$, $HO-CH_2-$, those represented by $R^5SO_3-CH_2-$ wherein $R^5$ has the same meaning as defined above, and $CH_3OCH_2OCH_2-$.

Examples of the "lower alkyl groups" represented by R', R" and R'" are straight chain or branched alkyl groups having 1 to 4 carbon atoms (e.g., methyl, ethyl, n-propyl, isopropyl, n-butyl, isobutyl, sec-butyl and tert-butyl). Examples of the "lower alkoxy groups" represented by R', R" and R'" are straight chain or branched alkoxy group having 1 to 4 carbon atoms (e.g., methoxy, ethoxy, n-propoxy, isopropoxy, n-butoxy, isobutoxy, sec-butoxy and tert-butoxy). R', R" and R'" are preferably methyl for R' and R" and isopropoxy for R'".

The definition of $R^5$ in the above mentioned group is explained in details hereinafter.

Examples of the aliphatic hydrocarbon residues for the "optionally substituted aliphatic hydrocarbon residues" represented by $R^{3'}$ are alkyl, cycloalkyl, alkenyl and alkynyl.

Examples of the alkyl groups are straight chain or branched alkyl groups having 1 to 12 carbon atoms, such as methyl, ethyl, n-propyl, isopropyl, n-butyl, isobutyl, sec-butyl, tert-butyl, heptyl, octyl, nonyl, decyl and dodecyl, among which lower alkyl groups having 1 to 4 carbon atoms (e.g., methyl, ethyl, n-propyl, isopropyl, n-butyl, isobutyl, sec-butyl and tert-butyl) are preferred.

Examples of the cycloalkyl groups are cycloalkyl groups having 3 to 8 carbon atoms such as cyclopropyl, cyclobutyl, cyclopentyl, cyclohexyl, cycloheptyl and cyclooctyl, among which cycloalkyl groups having 3 to 6 carbon atoms (e.g., cyclopropyl, cyclobutyl, cyclopentyl and cyclohexyl) are preferred.

Examples of the alkenyl groups are alkenyl groups having 2 to 4 carbon atoms such as vinyl, propenyl and butenyl, among which alkenyl groups having 2 or 3 carbon atoms (e.g., vinyl and propenyl) are preferred.

Examples of the alkynyl groups are alkynyl groups having 2 to 4 carbon atoms such as ethynyl, propynyl and butynyl, among which alkynyl groups having 2 or 3 carbon atoms (e.g., ethynyl and propynyl) are preferred.

Examples of aromatic hydrocarbon residues for the "optionally substituted aromatic hydrocarbon residues" represented by $R^{3'}$ are aryl groups having 6 to 14 carbon atoms. Examples of the aryl groups are phenyl, naphthyl, biphenylyl, anthryl and indenyl, among which aryl groups having 6 to 10 carbon atoms (e.g., phenyl and naphthyl) are preferred.

Examples of the aromatic heterocyclic groups for the "optionally substituted aromatic heterocyclic groups" represented by $R^{3'}$ are aromatic heterocyclic groups having at least one hetero atom selected from nitrogen atom, sulfur atom and oxygen atom. The aromatic heterocyclic groups may be condensed with a benzene ring or a 5- or 6-membered heterocycle. Examples of the aromatic heterocyclic groups are aromatic heterocyclic groups such as imidazolyl, triazolyl, tetrazolyl, pyrazolyl, pyridyl, thiazolyl, thiadiazolyl, thienyl, furyl, pyrrolyl, pyrazinyl, pyrimidinyl, oxazolyl and isoxazolyl, and condensed aromatic heterocyclic groups such as benzimidazolyl, imidazopyrimidinyl, imidazopyridinyl, imidazopyrazinyl, imidazopyridazinyl, benzothiazolyl, quinolyl, isoquinolyl, quinazolinyl and indolyl, among which 5- or 6-membered aromatic heterocyclic groups having 1 to 3 hetero atoms optionally selected from nitrogen atom, sulfur atom and oxygen atom (e.g., imidazolyl, triazolyl, thiazolyl, thiadiazolyl, thienyl, furyl, pyridyl and pyrimidinyl) are preferred.

Examples of the substituents for the "optionally substituted aliphatic or aromatic hydrocarbon residues" and the "optionally substituted aromatic heterocyclic groups" represented by $R^{3'}$ are hydroxyl group, optionally esterified carboxyl group (e.g., carboxyl, or alkoxycarbonyl group having 1 to 6 carbon atoms such as methoxycarbonyl, ethoxycarbonyl and butoxycarbonyl), nitro group, amino group, acylamino group (e.g., alkanoylamino group having 1 to 10 carbon atoms such as acetylamino, propionylamino and butyrylamino), amino group which is mono- or di-substituted with alkyl group having 1 to 10 carbon atoms (e.g., methylamino, dimethylamino, diethylamino and dibutylamino), optionally substituted 5- or 6-membered heterocyclic group (e.g., pyrrolidinyl, morpholino, piperidino, pyrazolydinyl, perhydroazepinyl, piperazinyl, 4-benzylpiperazinyl, 4-acetylpiperazinyl, 4-(4-trifluoromethoxyphenyl)-1-piperazinyl, 4-[4-(1,1,2,2-tetrafluoroethoxy)phenyl]-1-piperazinyl, 4-[4-(2,2,3,3-tetrafluoropropoxy)phenyl]-1-piperazinyl, 4-[4-(2,2,2-trifluoroethoxy)phenyl]-1-piperazinyl, 4-[4-(2,2,3,3,3-pentafluoropropoxy)phenyl]-1-piperazinyl and 4-(4-trifluoromethylphenyl)-4-piperazinyl), alkoxy group having 1 to 6 carbon atoms (e.g., methoxy, ethoxy, propoxy and butoxy), halogen atom (e.g., fluorine, chlorine and bromine), halogeno $C_{1-6}$ alkyl group (e.g., trifluoromethyl, dichloromethyl and trifluoroethyl), halogeno $C_{1-6}$ alkoxy group (e.g., trifluoromethoxy, 1,1,2,2-tetrafluoroethoxy, 2,2,2-trifluoroethoxy, 2,2,3,3-tetrafluoropropoxy, 2,2,3,3,3-pentafluoropropoxy, 2,2,3,3,4,4,5,5-octafluoropentoxy and 2-fluoroethoxy), oxo group, thioxo group, mercapto group, alkylthio group having 1 to 6 carbon atoms (e.g., methylthio, ethylthio and butylthio), alkylsulfonyl group having 1 to 6 carbon atoms (e.g., methanesulfonyl, ethanesulfonyl and butanesulfonyl) and alkanoyl group having 1 to 10 carbon atoms (e.g., acetyl, formyl, propionyl and butyryl). The number of the substituents described above is preferably 1 to 3, more preferably 1 or 2.

Preferably, $R^{3'}$ is an aryl group having 6 to 10 carbon atoms optionally substituted with a halogeno $C_{1-6}$ alkoxy group. More preferably, $R^{3'}$ is a phenyl group substituted with a halogeno $C_{1-6}$ alkoxy group, among which 4-(2,2,3,3-tetrafluoropropoxy)phenyl or 4-(1,1,2,2-tetrafluoroethoxy)phenyl is particularly preferred.

Examples of the lower alkyl groups as the substituent for the methine groups optionally substituted with a lower alkyl group represented by Y or Z include straight chain or branched alkyl groups having 1 to 4 carbon atoms (e.g., methyl, ethyl, n-propyl, isopropyl, n-butyl, isobutyl, sec-butyl and tert-butyl), among which methyl is preferable. Examples of the methine groups optionally substituted with a lower alkyl group represented by Y and Z are methine, ethylidyne, propylidyne and butylidyne, among which methine and ethylidine are preferred, and methine is the most preferred.

Further, it is preferred that Y and Z are, the same or different, a nitrogen atom or a methine group, and more preferably, one of which is a nitrogen atom and another is a methine group or the both are methine groups.

Examples of the "lower alkyl groups" represented by $R^5$ are straight chain or branched alkyl groups having 1 to 4 carbon atoms (e.g., methyl, ethyl, n-propyl, isopropyl, n-butyl, isobutyl, sec-butyl and tert-butylmethyl), among which methyl is preferable.

Examples of the "optionally substituted phenyl groups" represented by $R^5$ are phenyl, p-tolyl, p-chlorophenyl and p-nitrophenyl, among which p-tolyl is preferable.

$R^5$ is preferably methyl.

Examples of the "halogen atoms" represented by X, $X^2$, $X^3$ and $X^4$ are chlorine, bromine and iodine, among which chlorine and bromine are preferable.

$X^4$ represents a halogen atom or a group represented by $R^5SO_3$— wherein $R^5$ has the same meaning as defined above, and $X^4$ is preferably a halogen atom.

Examples of preferable compounds of the formula (I) include:

2-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl]-3(2H,4H)-1,2,4-triazolone, 4-[(1R,2R)-2-(2,4-difluorophenyl)-2-hydroxy-1-methyl-3-(1H-1,2,4-triazol-1-yl)propyl]-2-[4-(2,2,3,3-tetrafluoropropoxy)phenyl]-3(2H,4H)-1,2,4-triazolone, 4-[(1R,2R)-2-(2,4-difluorophenyl)-2-hydroxy-1-methyl-3-(1H-1,2,4-triazol-1-yl)propyl]-2-[4-(1,1,2,2-tetrafluoroethoxy)phenyl]-3(2H,4H)-1,2,4-triazolone, 2-[(1R,2R)-2-(2,4-difluorophenyl)-2-hydroxy-1-methyl-3-(1H-1,2,4-triazol-1-yl)propyl]-5-methyl-4-[4-(1,1,2,2-tetrafluoroethoxy)phenyl]-3(2H,4H)-1,2,4-triazolone, 1-[(1R,2R)-2-(2,4-difluorophenyl)-2-hydroxy-1-methyl-3-(1H-1,2,4-triazol-1-yl)propyl]-3-[4-(2,2,3,3-tetrafluoropropoxy)phenyl]-2(1H,3H)-imidazolone, 1-[(1R,2R)-2-(2,4-difluorophenyl)-2-hydroxy-1-methyl-3-(1H-1,2,4-triazol-1-yl)propyl]-3-[4-(1,1,2,2-tetrafluoroethoxy)phenyl]-2(1H,3H)-imidazolone, 1-[(1R,2R)-2-(2-fluorophenyl)-2-hydroxy-1-methyl-3-(1H-1,2,4-triazol-1-yl)propyl]-3-[4-(2,2,3,3-tetrafluoropropoxy)phenyl]-2(1H,3H)-imidazolone, and 1-[(1R,2R)-2-(2-fluorophenyl)-2-hydroxy-1-methyl-3-(1H-1,2,4-triazol-1-yl)propyl]-3-[4-(1,1,2,2-tetrafluoroethoxy)phenyl]-2(1H,3H)-imidazolone.

Examples of preferable compounds of the formula (I') include:

1-[(1R,2R)-2-(2,4-difluorophenyl)-2-hydroxy-1-methyl-3-(1H-1,2,4-triazol-1-yl)propyl]-3-[4-(2,2,3,3-tetrafluoropropoxy)phenyl]-2-imidazolidinone, 1-[(1R,2R)-2-(2,4-difluorophenyl)-2-hydroxy-1-methyl-3-(1H-1,2,4-triazol-1-yl)propyl]-3-[4-(1,1,2,2-tetrafluoroethoxy)phenyl]-2-imidazolidinone, 1-[(1R,2R)-2-(2-fluorophenyl)-2-hydroxy-1-methyl-3-(1H-1,2,4-triazol-1-yl)propyl]-3-[4-(2,2,3,3-tetrafluoropropoxy)phenyl]-2-imidazolidinone, and 1-[(1R,2R)-2-(2-fluorophenyl)-2-hydroxy-1-methyl-3-(1H-1,2,4-triazol-1-yl)propyl]-3-[4-(1,1,2,2-tetrafluoroethoxy)phenyl]-2-imidazolidinone.

The following scheme represents the method of preparing the compound of the formulae (I) and (I') through optically active intermediates for synthesizing the compound of the formulae (I) and (I'), provided by the present invention.

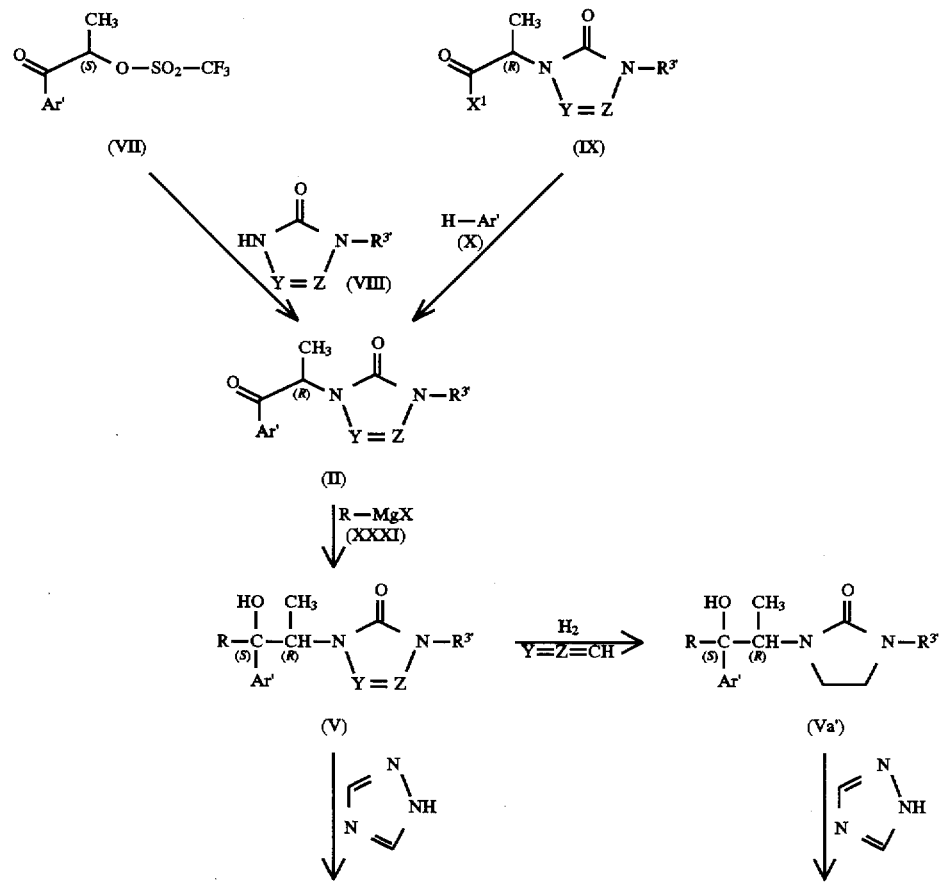

-continued

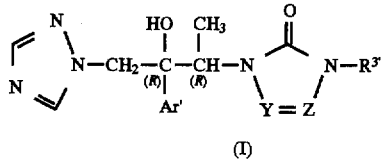
(I)

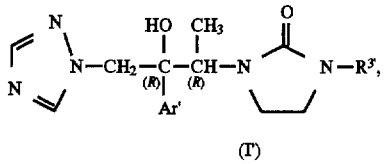
(I')

wherein $X^1$ is a halogen atom (e.g., chlorine, bromine and iodine) and the other symbols have the same meanings as defined above.

The compounds (I) and (I') or salts thereof can be prepared by reacting the compounds (V) and (Va') with 1H-1, 2,4-triazole or a salt thereof (e.g., alkali metal salt such as sodium salt, potassium salt, etc.).

In use of a compound wherein R of the compound of the formulae (V) and (Va') (referred to as the compounds (V) and (Va'), hereinafter) is HO—CH$_2$—, i.e., a compound of the formulae (V') and (Va") (referred to as the compounds (V') and (Va"), hereinafter), it is preferable that the compounds (V') and (Va") which are activated on its hydroxyl group upon necessity are reacted with 1H-1,2,4-triazole or a salt thereof.

By activating the hydroxyl group of the compounds (V'), and (Va") i.e., compounds wherein R of the compounds (V) and (Va') is HO—CH$_2$—, compounds wherein R of the compounds (V) and (Va') is a group represented by L—CH$_2$— (wherein L is an activated hydroxyl group) (referred to as the compounds (V") and (Va'"), hereinafter) are prepared. When the hydroxyl group of the compounds (V') and (Va") is activated prior to reacting the compounds (V') and (Va") with 1H-1,2,4-triazole or a salt thereof, the resulting compounds (V") and (Va'") may or may not be isolated before the reaction.

It is preferred that the hydroxyl group is activated using a compound of the formula (XIII) (referred to as the compound (XIII), hereinafter):

$$R^5SO_2X^4 \quad\quad (XIII)$$

wherein $R^5$ is a lower alkyl group or an optionally substituted phenyl group, and $X^4$ is a halogen atom or a group represented by $R^5SO_3$— wherein $R^5$ has the same meaning as defined above as an activating agent. By activating compounds (V') and (Va") with the compound (XIII), compounds wherein L of the compounds (V") and (Va'") is a group represented by $R^5SO_3$— ($R^5$ has the same meaning as defined above), i.e., compounds wherein R of the compounds (V) and (Va') is a group represented by $R^5SO_3$—CH$_2$— (referred to as the compounds (VI) and (VI'), hereinafter):

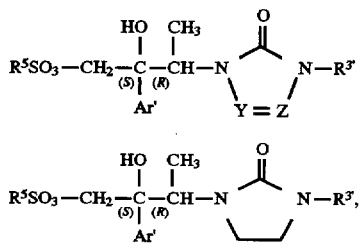

wherein the symbols have the same meanings as defined above, are prepared. The reaction of the compounds (V') and (Va") with the compound (XIII) can be conducted in a solvent which does not impede the reaction in the presence of a base.

Preferably, the compound (XIII) is reacted with 1 mole of the compounds (V') and (Va") in an amount of about 1 to 2 moles, more preferably about 1.0 to 1.5 moles. Examples of the bases used in the above reaction are preferably organic bases such as triethylamine, pyridine and diisopropyl ethylamine. The use amount of the base is preferably about 1 to 2 times by mole, more preferably about 1 to 1.5 times by mole, to the compounds (V') and (Va").

Examples of the solvents which do not impede the reaction are ketones such as acetone; nitriles such as acetonitril; hydrocarbons such as benzene, toluene and hexane; halogenated hydrocarbons such as dichloromethane and chloroform; esters such as ethyl acetate; and ethers such as diethyl ether. They may be used either singly or as a mixture thereof in a suitable mixing ratio.

In the reaction of the compounds (V') and (Va") with the compound (XIII), the reaction temperature is preferably from about −10° to 40° C., more preferably from about 0° to 10° C. The reaction time is preferably from about 0.1 to 1 hour, more preferably from about 0.2 to 0.5 hours.

The compounds (VI) and (VI') which is produced by the reaction described above may not be isolated from the reaction mixture before reacting the compounds (VI) and (VI') with 1H-1,2,4-triazole or a salt thereof. However, it is preferred to isolate the compounds (VI) and (VI') before the reaction.

When preparing the compounds (I) and (I') from the compounds (V") and (Va'") wherein R of the compounds (V) and (Va') is L—CH$_2$— wherein L is an activated hydroxyl group, the compounds (I) and (I') or salts thereof are prepared by reacting the compounds (V") and (Va'") with 1H-1,2,4-triazole or a salt thereof.

The reaction of the compounds (V") and (Va'") with 1H-1,2,4-triazole or a salt thereof proceeds by using 1H-1, 2,4-triazole or a salt thereof in an amount of about 1 to 10 moles, preferably about 2 to 6 moles, to 1 mole of the compounds (V") and (Va'").

The reaction is usually conducted in a solvent which does not impede the reaction. Examples of the solvents are ketones such as acetone; sulfoxides such as dimethyl sulfoxide; ethers such as diethyl ether, tetrahydrofuran and dioxane; nitriles such as acetonitrile; aromatic hydrocarbons such as benzene, toluene and xylene; halogenated hydrocarbons such as dichloromethane, chloroform and 1,2-dichloroethane; esters such as ethyl acetate; and amides such as dimethylformamide, acetamide, dimethylacetamide, 1-methyl-2-pyrrolidone and 1,3-dimethyl-2-imidazolidinone, among which sulfoxides such as dimethylsulfoxide, and amides such as dimethylformamide, acetamide, dimethylacetamide, 1-methyl-2-pyrrolidone and 1,3-dimethyl-2-imidazolidinone are preferred, and amides such as dimethylformamides, acetamide, dimethylacetamide, 1-methyl-2-pyrrodidone and 1,3-dimethyl-2-imidazolidinone are more preferred, and dimethylformamide is particularly preferred. They may be used either singly or as a mixture thereof in a suitable mixing ratio.

The use amount of the solvent is about 100 times or less by weight, preferably about 1 to 50 times by weight, more preferably about 10 to 20 times by weight, to the compounds (V''') and (Va''').

In the reaction of the compounds (V''') and (Va''') with 1H-1,2,4-triazole or a salt thereof, the reaction temperature is preferably from about 40° to 120° C., more preferably from about 70° to 100° C. The reaction time is preferably from about 1 to 10 hours, more preferably from about 2 to 8 hours.

Further, it is preferred that the above reaction is conducted in the presence of a base such as an alkali metal carbonate, alkali metal hydrogencarbonate, alkali metal hydroxide, alkali metal hydride, alkali metal organic carboxylate, alkali metal alcoholate and tetrabutylammonium fluoride. Preferably, it is conducted in the presence of an alkali metal carbonate, alkali metal hydrogencarbonate or alkali metal hydroxide, more preferably alkali metal carbonate or alkali metal hydrogencarbonate, and most preferably alkali metal carbonate.

Examples of the alkali metal carbonates include lithium carbonate, sodium carbonate, potassium carbonate and cesium carbonate, among which potassium carbonate is preferable. Examples of the alkali metal hydrogencarbonates include lithium hydrogencarbonate, sodium hydrogencarbonate and potassium hydrogencarbonate. Examples of the alkali metal hydroxides include lithium hydroxide, potassium hydroxide and sodium hydroxide. Examples of the alkali metal hydrides include potassium hydride and sodium hydride. Examples of the alkali metal organic carboxylates include sodium acetate. Examples of the alkali metal alcoholates include sodium methylate and potassium tert-butylate.

The use amount of the base is preferably about 1 to 20 times by mole, more preferably about 3 to 10 times by mole, to the compound of the formulae (V''') and (Va''').

A method for adding the base is not specifically limited. For example, the base may be added after adding 1H-1,2,4-triazole or salt thereof and the compounds (V''') and (Va''') to the solvent, or the compounds (V''') and (Va''') and 1H-1,2,4-triazole or salt thereof are added to a mixture prepared by adding the base to the solvent, or the compounds (V''') and (Va'''), 1H-1,2,4-triazole or a salt thereof, and the base are added to the solvent in sequence. Further, the compounds (V''') and (Va''') and the base may be added to the solvent, then the mixture is heated at about 20° to 40° C. for about 30 minutes to 1 hour, followed by adding 1H-1,2,4-triazole or a salt thereof.

A compound of the formulae (XIV) and (XIV'):

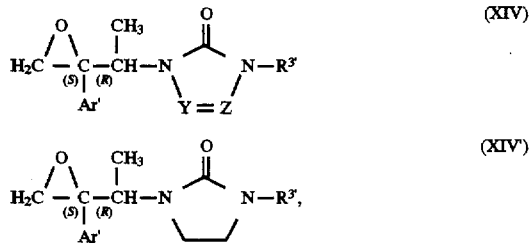

wherein the symbols have the same meanings as defined above, is prepared by adding the compounds (V''') and (Va''') and the base to the solvent and then heating the mixture at about 20° to 40° C. for 0.5 to 1 hour. The obtained compounds (XIV) and (XIV') may be isolated before reacting with 1H-1,2,4-triazole or a salt. In this case, the reaction can be conducted in the presence or absence, preferably in the presence of the base by adding the compound (XIV) or (XIV') and 1H-1,2,4-triazole or a salt thereof to the solvent.

Preferably, the compound (V) is a compound wherein R is a group represented by HO—CH$_2$— or R$^5$SO$_3$—CH$_2$— wherein R$^5$ is a lower alkyl group or an optionally substituted phenyl group.

The compounds (I) and (I') or salts thereof given by the above method can be isolated and purified from the reaction mixture by known isolation and purification procedure per se such as extraction, concentration, neutralization, filtration, recrystallization and chromatography.

The compounds (I) and (I') can be also used as salts, and examples of such salts are pharmaceutically-acceptable salts such as salts with inorganic acid (e.g., hydrochloric acid, hydrobromic acid, sulfuric acid, nitric acid and phosphoric acid) or organic acid (e.g., acetic acid, tartaric acid, citric acid, fumaric acid, maleic acid, p-toluene-sulfonic acid and methanesulfonic acid).

The salt of the compounds (I) and (I') can be manufactured by a known method per se such as by adding the above-mentioned inorganic or organic acid to the compound of the formulae (I) and (I').

The compound (Va') can be prepared by submitting the compound (V) to reduction reaction, preferably to catalytic hydrogenation. The catalytic hydrogenation of the compound (V) can be conducted in a solvent which does not impede the reaction in the presence of a catalysis.

Examples of the solvents which do not impede the reaction are ketones such as acetone and methyl ethyl ketone; alcohols such as methanol, ethanol, propanol, isopropyl alcohol and butanol; esters such as ethyl acetate; hydrocarbons such as benzene, toluene, hexane and xylene; carboxylic acids such as acetic acid and propionic acid. They may be used either singly or as a mixture thereof in a suitable mixing ratio.

Examples of the preferred catalyst are metal catalysts such as palladium carbon, platinum oxide and platinum carbon, and palladium carbon is more preferred.

The catalytic hydrogenation of the compound (V) can be carried out under ordinary pressure at ca.150 kg/cm$^2$, and the reaction temperature is from room temperature to ca.100° C.

The compound (V) can be produced by reacting a compound of the formula (II) (referred to as the compound (II), hereinafter) with a Grignard reagent of the formula (XXXI) (referred to as the compound (XXXI), hereinafter).

Examples of the Grignard reagents used in the present invention are a compound of the formula (XI) (referred to as the compound (XI)), a compound of the formula (XII) (referred to as the compound (XII), hereinafter), (diisopropoxymethylsilyl)methyl magnesium chloride, and CH$_3$OCH$_2$OCH$_2$MgCl, among which the compound (XI) and the compound (XII) are preferred and more preferable is the compound (XI).

In use of the compound (XI) as a Grignard reagent, the compound (I) is produced by, for example, a method as given in the following scheme:

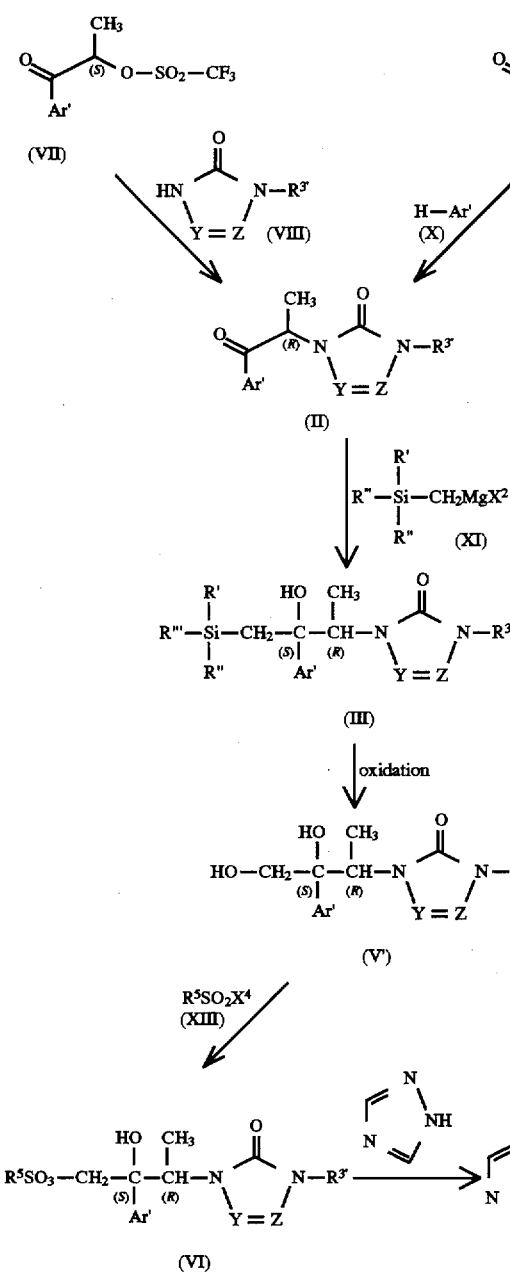

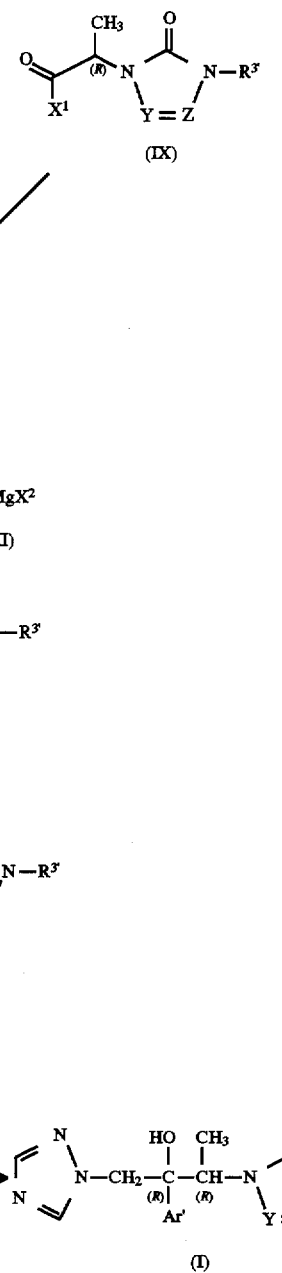

In use of the compound (XI) as a Grignard reagent, the compound (V') is produced by reacting the compound (II) with the compound (XI) and oxidizing the resultant. More particularly, the compound (V') is produced by:

reacting the compound (II) with the compound (XI) in a solvent which does not impede the reaction to give a compound of the formula (III) (referred to as the compound (III), hereinafter):

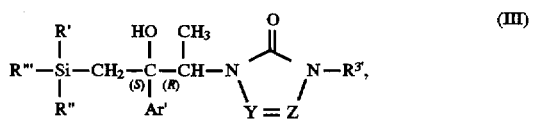

wherein the symbols have the same meanings as defined above; and then reacting the obtained compound (III) with an oxidizing agent in a solvent which does not impede the reaction. The compound (III) which is produced by the reaction of the compound (II) with the compound (XI) may or may not be isolated before reacting with an oxidizing agent.

The reaction of the compound (II) with the compound (XI) proceeds by using the compound (XI) in an amount of about 1 to 10 moles, preferably about 1 to 3 moles to 1 mole of the compound (II). Examples of the solvents used in the above reaction are ethers such as diethyl ether, tetrahydrofuran and dioxane; hydrocarbons such as benzene, toluene, xylene, hexane and petroleum ether; halogenated hydrocarbons such as dichloromethane, chloroform and 1,2-dichloroethane; and the like. They may be used either singly or as a mixture thereof in a suitable mixing ratio.

Preferably, the reaction of the compound (II) with the compound (XI) proceeds by adding a solution of the compound (XI) (preferably in ethers such as diethyl ether and tetrahydrofuran) to a solution of the compound (II) (in a solvent which does not impede the reaction as mentioned above), or adding a solution of the compound (II) (in a solvent which does not impede the reaction as mentioned above) to a solution of the compound (XI) (preferably in ethers such as diethyl ether and tetrahydrofuran).

In the reaction of the compound (II) with the compound (XI), the reaction temperature is suitably from about −40° to about 40° C., preferably from about −20° to about 25° C. The reaction time is suitably from about 0.1 to about 10 hours, preferably from about 0.2 to about 1 hour.

The reaction of the compound (III), which is produced by the reaction of the compound (II) with the compound (XI), with the oxidizing agent proceeds by using the oxidizing agent in an amount about 1 to 20 moles, preferably about 5 to 10 moles to 1 mole of the compound (III). The oxidizing agent used in the reaction is preferably an aqueous solution of hydrogen peroxide. Examples of the solvents which do not impede the reaction are water; alcohols such as methanol and ethanol; ethers such as tetrahydrofuran; and the like. They may be used either singly or as a mixture thereof in a suitable mixing ratio.

It is preferred that the reaction of the compound (III) with the oxidizing agent is conducted in the presence of a base. Preferably, the base may be sodium hydrogencarbonate, potassium hydrogencarbonate, sodium carbonate and potassium carbonate, more preferably, the base is sodium hydrogencarbonate.

In the reaction of the compound (III) with the oxidizing agent, the reaction temperature is suitably from about 20° to about 100° C., preferably from about 70° to about 80° C. The reaction time is suitably from about 0.5 to about 8 hours, preferably from about 0.5 to about 2 hours.

Preferably, the compound (XI) is a compound wherein R' and R" are a methyl group and R'" is $(CH_3)_2CHO$—.

When the compound (XII) is used as a Grignard reagent, the compound (I) can be produced by, for example, a method as given in the following scheme:

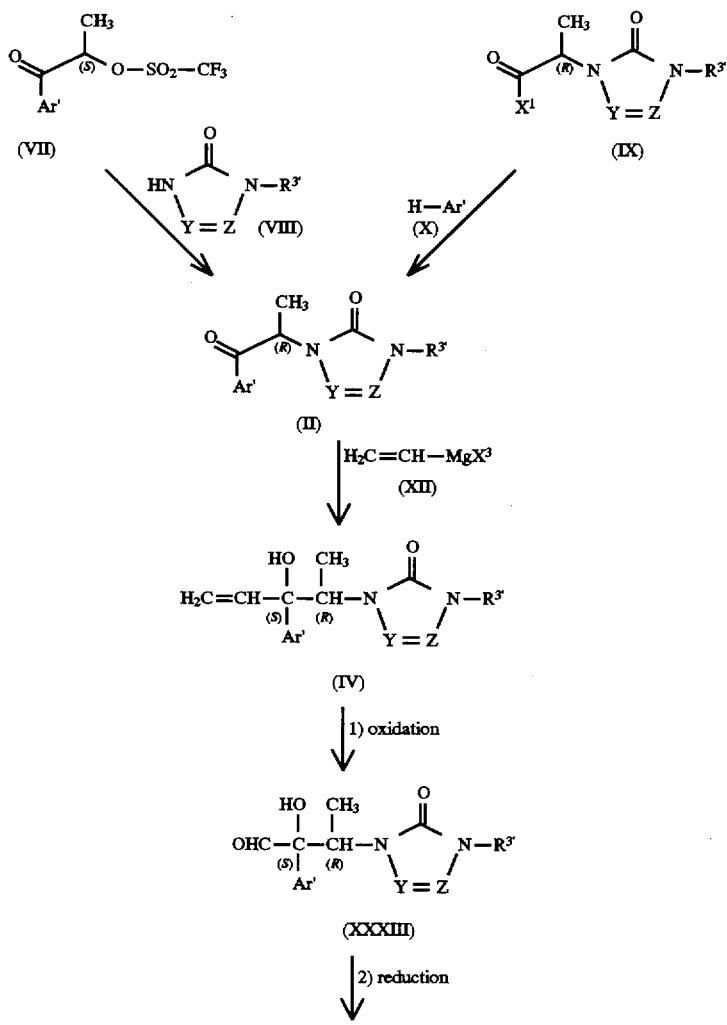

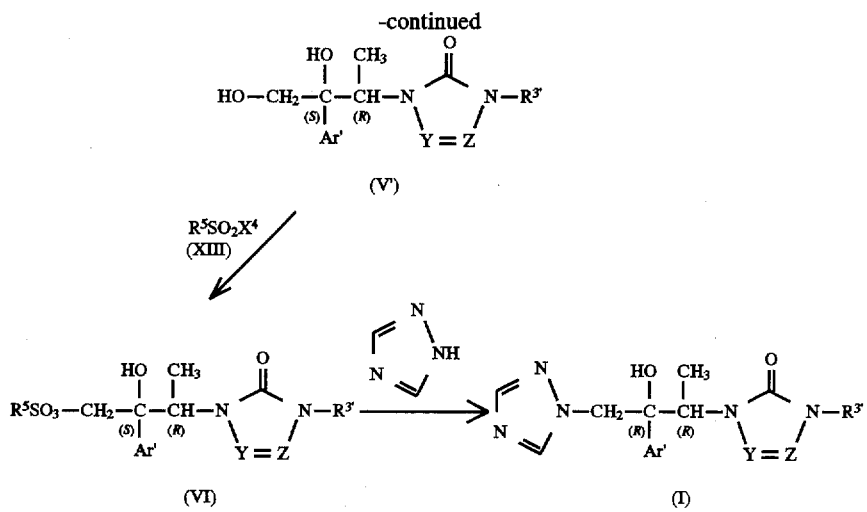

-continued (V')

(VI) → (I)

In use of the compound (XII) as a Grignard reagent, the compound (V') can be produced by reacting the compound (II) with the compound (XII) and oxidizing the resultant, followed by reducing. More particularly, the compound (V') is produced by:

reacting the compound (II) with the compound (XII) in a solvent which does not impede the reaction to give a compound of the formula (IV) (referred to as the compound (IV), hereinafter):

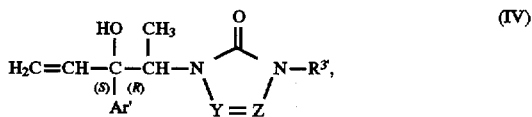

wherein the symbols have the same meanings as defined above;

reacting the obtained compound (IV) with an oxidizing agent in a solvent which does not impede the reaction to give a compound of the formula (XXXIII) (referred to as the compound (XXXIII):

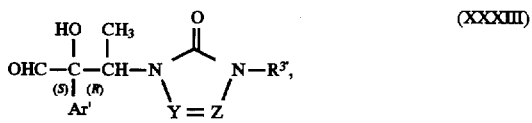

wherein the symbols have the same meanings as defined above (referred to as the first stage, hereinafter); and then reacting the obtained compound (XXXIII) with a reducing agent in a solvent which does not impede the reaction (referred to as the second stage, hereinafter). The compound (IV) which is produced by the reaction of the compound (II) with the compound (XII) may or may not be isolated before reacting with the oxidizing agent. The compound (XXXIII) which is produced by the reaction of the compound (IV) with the oxidizing agent may or may not be isolated before reacting with the reducing agent.

The reaction of the compound (II) with the compound (XII) proceeds by using the compound (XII) in an amount of about 1 to 7 moles, preferably about 1 to 2 moles, to 1 mole of the compound (II). Examples of the solvents which do not impede the reaction are ethers such as diethyl ether, tetrahydrofuran and dioxane; hydrocarbons such as benzene, toluene, xylene, hexane and petroleum ether; halogenated hydrocarbons such as dichloromethane, chloroform and 1,2-dichloroethane; and the like. They may be used either singly or as a mixture thereof in a suitable mixing ratio.

The reaction of the compound (II) with the compound (XII) is preferably conducted by adding a solution of the compound (XII) (preferably in ethers such as diethyl ether and tetrahydrofuran) to a solution of the compound (II) (in a solvent which does not impede the reaction as mentioned above), or adding the solution of the compound (II) (in a solvent which does not impede the reaction as mentioned above) to a solution of the compound (XII) (preferably in ethers such as diethyl ether and tetrahydrofuran).

In the reaction of the compound (II) with the compound (XII), the reaction temperature is suitably from about −40° to about 30° C., preferably from about −20° to about 0° C. The reaction time is suitably from about 0.1 to about 2 hours, preferably from about 0.2 to about 0.5 hours.

Examples of the oxidizing agents used at the first stage of the conversion reactions of the compound (IV) to the compound (V') are sodium metaperiodate in the presence of osmium tetroxide, and ozone.

In use of sodium metaperiodate in the presence of osmium tetroxide, the use amount of osmium tetroxide is preferably about 0.005 to 0.2 times by mole, more preferably about 0.01 to 0.05 times by mole, to the compound (IV). The use amount of sodium metaperiodate is preferably about 1 to 10 times by mole, more preferably about 1 to 5 times by mole, to the compound (IV). In use of sodium metaperiodate in the presence of osmium tetroxide as the oxidizing agent, examples of the solvents which do not impede the reaction are preferably water; alcohols such as methanol and ethanol; and the like. They may be used either singly or as a mixture thereof in a suitable mixing ratio. In use of sodium metaperiodate in the presence of osmium tetroxide as the oxidizing agent, the reaction temperature is suitably from about 0° to about 40° C., preferably from about 15 to about 25° C., and the reaction time is suitably from about 1 to about 48 hours, preferably from about 4 to about 24 hours.

In use of ozone as the oxidizing agent, preferable examples of the solvents which do not impede the reaction are halogenated hydrocarbons such as dichloromethane and 1,2-dichloroethane; hydrocarbons such as hexane and pentane; and the like. They may be used either singly or as a mixture thereof in a suitable mixing ratio. The reaction temperature in oxidation with ozone is suitably from about −100° to about 0° C., preferably from about −80° to about −30° C., and the reaction time is suitably from about 0.1 to about 24 hours. In the oxidation reaction with ozone, it is necessary to add sulfides such as dimethyl sulfide to the reaction solution after confirming completion of the reaction. The amount of the sulfide is about 1 to 20 times by mole, preferably about 2 to 10 times by mole, to the compound (IV). After adding the sulfide, it is preferred that the reaction solution is allowed to stand at about −80° to 20° C., preferably about −40° to 0° C., for 0.1 to 2 hours, preferably about 0.2 to 1 hour.

The amount of the reducing agent used at the second stage of the conversion reactions of the compound (IV) to the compound (V') is about 1 to 10 moles, preferably about 1 to 3 moles, to the compound (IV). Examples of the reducing agents are sodium borohydride, sodium lithium hydride and lithium borohydride.

Examples of the solvents which do not impede the reaction used at the second stage are water; alcohols such as methanol and ethanol; ethers such as diethyl ether and tetrahydrofuran; and the like. They are properly selected depending on the sort of the reducing agent, and may be used either singly or as a mixture thereof in a suitable mixing ratio.

At the second stage, the reaction temperature is suitably from about 0° to about 40° C., preferably from about 0° to about 30° C., and the reaction time is su to about 2 hours, preferably from about 0.1 to about 0.5 hours.

The compound (II) can be produced by, for example, reacting the compound (VII) with the compound (VIII) or a salt thereof, or reacting the compound (IX) with the compound (X), as represented in the above scheme.

The reaction of the compound (VII) with the compound (VIII) or a salt thereof (e.g., alkali metal salt such as sodium salt and potassium salt) is conducted in a solvent which does not impede the reaction in the presence or absence of a base. In use of the compound (VIII) in the reaction, the use amount of the compound (VIII) is preferably about 1 to 5 moles, more preferably about 1 to 1.5 moles, to 1 mol of the compound (VII). Preferably, the reaction is conducted in the presence of a base such as sodium hydride, potassium hydride, sodium hydroxide, triethylamine, pyridine and diisopropylethylamine. The use amount of the base is preferably about 0.5 to 1 time by mole, more preferably about 0.9 to 1 time by mole, to the compound (VII). In use of a salt of the compound (VIII), the reaction is preferably conducted in the absence of the base. The use amount of the salt of the compound (VIII) is preferably about 0.5 to 1 time by mole, more preferably about 0.8 to 1 time by mole, to the compound (VII).

Examples of the solvents which do not impede the reaction used in the reaction of the compound (VII) with the compound (VIII) are ketones such as acetone; sulfoxides such as dimethyl sulfoxide; ethers such as diethyl ether, tetrahydrofuran and dioxane; nitriles such as acetonitrile; aromatic hydrocarbons such as benzene, toluene and xylene; halogenated hydrocarbons such as dichloromethane, chloroform and 1,2-dichloroethane; esters such as ethyl acetate; amides such as dimethylformamide, acetamide, dimethylacetamide, 1,3-dimethyl-2-imidazolidinone and 1-methyl-2-pyrrolidone; and the like. They may be used either singly or as a mixture thereof in a suitable mixing ratio.

In the reaction of the compound (VII) with the compound (VIII) or a salt thereof, the reaction temperature is suitably about −78° to about 30° C., preferably from about −50° to about 0° C. The reaction time is suitably from about 5 minutes to about 24 hours, preferably from about 20 minutes to about 4 hours.

The reaction of the compound (IX) with the compound (X) is conducted in the presence of a Lewis acid, in a solvent which does not impede the reaction or in the absence of the solvent. Preferably, the reaction proceeds by using the compound (X) in an amount of about 1 to 10 moles, more preferably about 1.5 to 3 moles, to 1 mole of the compound (IX). Examples of the Lewis acids are aluminum chloride, titanium tetrachloride, ferric chloride and tin tetrachloride. The amount of the Lewis acid used in the above reaction is preferably about 1 to 10 times by mole, more preferably about 1 to 3 times by mole, to the compound (IX).

In use of a solvent in the reaction of the compound (IX) with the compound (X), examples of the solvents are preferably halogenated hydrocarbons such as dichloromethane, chloroform and 1,2-dichloroethane; carbon disulfide; nitrobenzene; and the like. They may be used either singly or as a mixture thereof in a suitable mixing ratio.

In the reaction of the compound (IX) with the compound (X), the reaction temperature is suitably from about 0° to about 100° C., preferably from about 20° to about 60° C. The reaction time is suitably from about 0.5 to about 24 hours, preferably from about 2 to about 8 hours.

The optically active intermediates (II), (III), (IV), (V), (Va), (Va'), (V'), (Va''), (V''), (Va'''), (VI), (VI'), (XIV), (XIV') and (XXXIII) can be isolated and purified from the reaction mixture by a known procedure per se such as extraction, concentration, neutralization, filtration, recrystallization, chromatography, etc.

The compound (VII) which is one of the starting compounds of the present invention can be synthesized by, for example, a method as given in the following scheme:

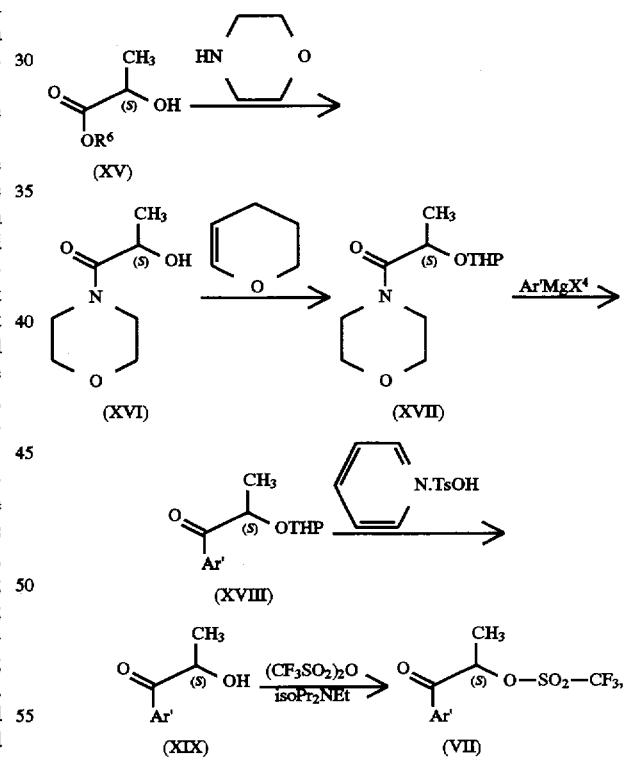

wherein $R^6$ is a $C_{1-4}$ lower alkyl group, THP is tetrahydropyranyl group, $X^4$ is a halogen atom, Ts is p-toluenesulfonyl group, Pr is propyl group, Et is ethyl group, and Ar' has the same meaning as defined above.

A method for synthesizing a compound wherein Ar' of the compound (XIX) in the above scheme is 2,4-difluorophenyl is described in Japanese Laid Open Patent Publication Hei 5 (1993)-230038.

The compound (XX) wherein $X^1$ of the compound (IX) which is another starting compound of the present invention is a chlorine atom can be synthesized by, for example, a method as given in the following scheme:

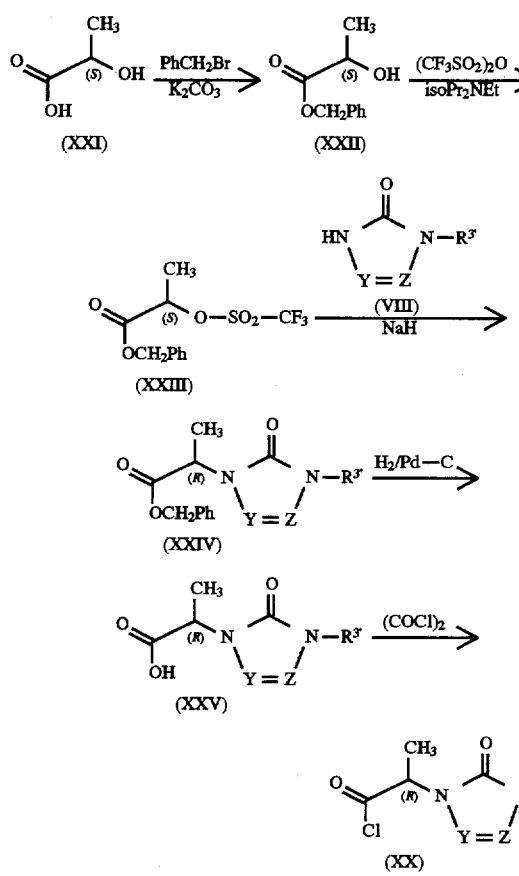

wherein Ph is a phenyl group and the other symbols have the same meanings as defined above.

The compound (IX) wherein $X^1$ is a halogen atom other than a chlorine atom can be produced in accordance with the method as described above by replacing $(COCl)_2$ with each halogenation agent (e.g., $(COBr)_2$ or $PBr_3$).

The compound (VIII) which is still another starting compound of the present invention or a salt thereof can be produced by a known method per se, for example, the method as described in or in accordance with European Laid-Open Patent Publication No. 567982. The compound (XXVI) wherein Y and Z of the compound (VIII) or a salt thereof are CH and N, respectively, or a salt thereof can be also produced by, for example, a method as given in the following scheme.

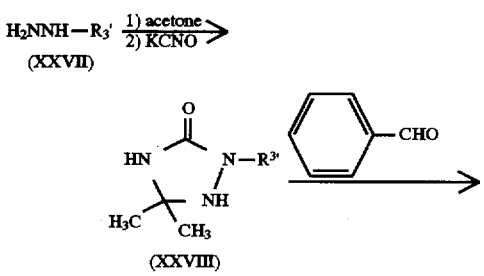

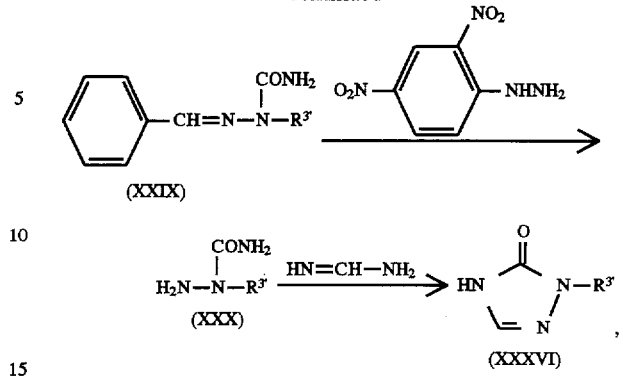

wherein the symbols have the same meanings as defined above.

The compounds (VII), (XX) and (XXVI) and their synthetic intermediates (XVI), (XVII), (XVIII), (XIX), (XXII), (XXIII), (XXIV), (XXV), (XXVIII), (XXIX) and (XXX) or salts thereof can be isolated and purified from the reaction mixture by a known procedure per se such as extraction, concentration, neutralization, filtration, recrystallization, chromatography, etc.

The optically active intermediates (II), (III), (IV) and (V) given in the present invention are derived from (S)-lactic acid (XXI) or its ester compound (XV) by chemical synthesis, and the optically active compounds (I) and (I') useful as an antifungal agent can be synthesized via those optically active intermediates. Accordingly, it is obvious that when conducting the same reaction as given in the above using (R)-lactic acid and (R)-lactic acid ester which are enantiomers of the compounds (XXI) and (XV), respectively, a (S, S)-compound which is an enantiomer of the compounds (I) and (I') can be synthesized via enantiomers corresponding to the compounds (II), (III), (IV) and (V), respectively.

The compounds (I) and (I') or salts thereof which are produced by the method of the present invention have a low toxicity and exhibit high antifungal activities with broad antifungal spectrum against various fungi (e.g., Candida, Aspergillus and Cryptococcous). Accordingly, they can be used for prevention or treatment of fungal infections (e.g., candidiasis, aspergillosis, cryptococcosis, etc) of mammals (e.g., human being, domestic animals, fowls and the like). In addition, the compounds (I) and (I') or salts thereof can be also used as an antifungal preparation for agricultural use.

The usage including the actual pharmacological effect, function, administration object, safety, specified object diseases, dosage, administration route and administration form as an antifungal agent for medical use, and usage as an antifungal preparation for agricultural use of the final compounds (I) and (I') are similar to those described in the above-mentioned European Laid-Open Patent Publication No. 567982.

PREFERRED EXAMPLES OF THE INVENTION

The present invention is further described by way of the following Working Examples.

$^1$H-NMR spectra were measured by a spectrometer of Varian Gemini 200 type (200 MHz) using tetramethylsilane as an internal standard. All δ values are given by ppm. In the mixing solvents, the figures given in ( ) are the mixing ratio of each of the solvents by volume. Unless otherwise specified, the symbol % means that by weight.

The symbols used in the examples have the following meanings.

s: singlet; d: doublet; t: triplet; q: quartet; dd: double doublet; dt: double triplet; tt: triple triplet; m: multiplet; quintet: quintet; septet: septet; br: broad; J: coupling constant.

Example 1

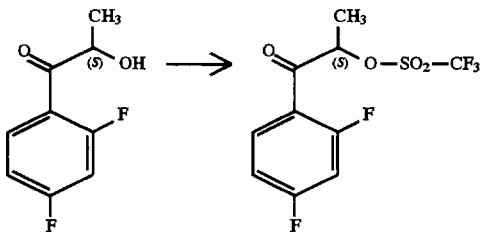

(2S)-2', 4'-Difluoro-2-hydroxypropiophenone (26.01 g: synthesized by the method disclosed in Japanese Laid Open Publication Hei 5-230038) was dissolved in 300 ml of dichloromethane, to which 19.90 g of diisopropylethylamine was added at −60° C. under nitrogen atmosphere. Then, to the mixture was added dropwise 25.90 ml of trifluoromethanesulfonic anhydride over the period of 20 minutes. After the reaction temperature was gradually raised to −30° C., the reaction solution was stirred for 30 minutes. The reaction mixture was purified by silica gel chromatography (silica gel: 400 g, eluent; dichloromethane:hexane=1:1) to give 39.21 g of (2S)-2', 4'-difluoro-2-trifluoromethanesulfonyloxypropiophenone as a pale yellow oil.

$^1$-NMR (CDCl$_3$) δ: 1.73 (3H, dd, J=7.0 Hz,1.6 Hz), 5.93 (1H,q,J=7.0 Hz), 6.90–7.12 (2H,m), 8.03 (1H,dt,J=6.4 Hz,8.6 Hz)

$[\alpha]_D^{23}$+29.2° (c=1.12, in methanol)

Example 2

(S)-Lactic acid (60 g) and 75 g of benzyl bromide were dissolved in 500 ml of dimethylformamide, to which 72.5 g of potassium iodide and 150 g of potassium carbonate were added with ice cooling. After the mixture was stirred at room temperature for 6 hours, 500 ml of ethyl acetate and 500 ml of diisopropyl ether were added thereto. The supernatant layer was obtained by decantation and the precipitate was washed with 100 ml of diisopropyl ether. The organic solutions thus obtained were combined and poured into 200 ml of 5N-hydrochloric acid under ice-cooling. The separated organic layer was washed with 250 ml of 2N-hydrochloric acid, 100 ml of an aqueous solution of sodium thiosulfate and 100 ml of an aqueous solution of sodium chloride successively, and dried over magnesium sulfate. After the solvent was distilled off under reduced pressure, the residue was distilled under reduced pressure to give 29.3 g of (S)-benzyl lactate (yield: 37%) as a colorless oil.

bp ca. 93° C./20 mmHg $^1$H-NMR (CDCl$_3$) δ: 1.43 (3H,d,J=7 Hz), 2.82 (1H,br), 4.32 (1H,g,J=7 Hz), 5.21 (2H,s), 7.28–7.45 (5H,m)

Example 3

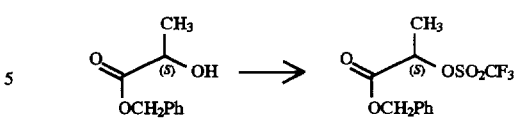

(S)-Benzyl lactate (29 g) and 22.8 g of diisopropyl ethylamine were dissolved in 300 ml of dichloromethane and the solution was cooled to −50° to −60° C. To the solution was added dropwise 50 g of trifluoromethanesulfonic anhydride over the period of 15 minutes and the reaction mixture was stirred at −30° to −20° C. for 10 minutes. After adding 200 ml of dichloromethane, the mixture was washed with 50 ml of water, 50 ml of an aqueous solution of sodium bicarbonate and an aqueous solution of sodium chloride successively. The organic layer was dried over magnesium sulfate. The solvent was distilled off under reduced pressure. The residue was purified by silica gel chromatography (silica gel: 250 g, eluent; hexane:dichloromethane=1:1) to give 44.2 g of benzyl (2S)-2-trifluoromethanesulfonyloxypropionate (yield: 88%) as a colorless oil.

$^1$H-NMR (CDCl$_3$) δ: 1.70 (3H,d,J=7 Hz), 5.26 (1H,q,J=7 Hz), 5.26 (2H,s), 7.31 (5H,s)

Example 4

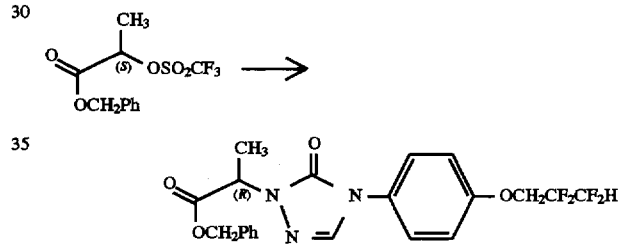

4-[4-(2,2,3,3-Tetrafluoropropoxy)phenyl]-3(2H,4H)-1,2,4-triazolone (18 g) was dissolved in 180 ml of dimethylformamide, to which 60% sodium hydride in oil (2.52 g) was added. The mixture was vigorously stirred at room temperature for 40 minutes. The reaction solution was added to a solution of 20 g of benzyl (2S)-2-trifluoromethanesulfonyloxypropionate prepared in Example 3 in 240 ml of tetrahydrofuran under nitrogen atmosphere at −40° to −30° C. over the period of ca. 40 minutes. The mixture was stirred at −40° to −20° C. for 40 minutes, to which 10 ml of acetic acid was added. Then, the reaction solution was diluted with a mixture of 100 ml of ethyl acetate and 500 ml of diisopropyl ether, washed with 250 ml of water, 2N-hydrochloric acid (250 ml×2) and 250 ml of an aqueous solution of sodium chloride successively. After dring over magnesium sulfate, the solvent was distilled off under reduced pressure. The residue was purified by silica gel chromatography (silica gel: 250 g, eluent; hexane:ethyl acetate=2:1) to give 24 g of benzyl (2R)-2-[4-[4-(2,2,3,3-tetrafluoropropoxy)phenyl]-4,5-dihydro-5-oxo-1H-1,2,4-triazol-1-yl]propionate (yield: 82%) as a colorless oil.

$^1$H-NMR (CDCl$_3$) δ: 1.76 (3H,d,J=7.4 Hz), 4.38 (2H,tt, J=11.8 Hz,J=1.4 Hz), 5.08 (1H,q,J=7.4 Hz), 5.20 (2H,s), 6.06 (1H,tt,J=53 Hz,J=4.6 Hz), 7.02 (2H,dt,J=9 Hz,J=2,2 Hz), 7.33 (5H,s), 7.47 (2H,dt,J=9 Hz,J=2.2 Hz), 7.66 (1H,s)

Example 5

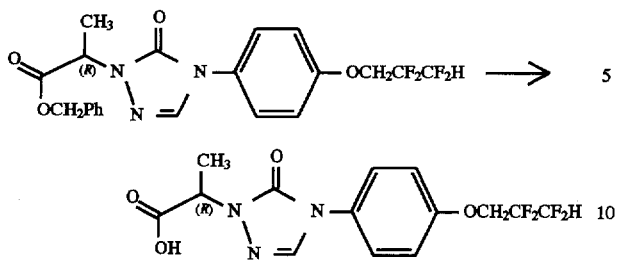

Benzyl (2R)-2-[4-[4-(2,2,3,3-tetrafluoropropoxy)phenyl]-4,5-dihydro-5-oxo-1H-1,2,4-triazol-1-yl]propionate (24 g) was dissolved in 500 ml of ethanol, to which 10% palladium-carbon (2.5 g: containing 50% of water) was added. The mixture was stirred under hydrogen atmosphere at room temperature for an hour.

After the catalyst was removed by filtration, the filtrate was concentrated under reduced pressure. The residue was recrystallized from a mixture of ethanol and diisopropyl ether to give 17.3 g of (2R)-2-[4-[4-(2,2,3,3-tetrafluoropropoxy)phenyl]-4,5-dihydro-5-oxo-1H-1,2,4-triazol-1-yl]propanoic acid as colorless prisms.

mp 162°–165° C.

$^1$H-NMR (DMSO-$d_6$) δ: 1.56 (3H,d,J=7.4 Hz), 4.65 (2H, tt, J=13.4 Hz,J=1.6 Hz), 4.85 (1H,q,J=7.4 Hz), 6.69 (1H,tt, J=52 Hz, J=5.5 Hz), 7.20 (2H,dt,J=9 Hz,J=2.2 Hz), 7.64 (2H,dt,J=9 Hz, J=2.2 Hz), 8.45 (1H,s)

$[\alpha]_D^{23}$+59.3° (c=1.0, in methanol)

Elemental analysis for $C_{14}H_{13}F_4N_3O_4$ Calcd: C 46.29, H 3.61, N 11.57 Found: C 46.37, H 3.67, N 11.53

Example 6

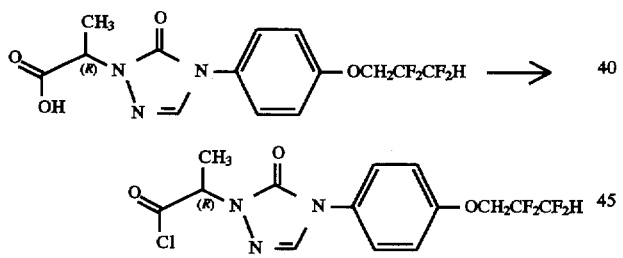

(2R)-2-[4-[4-(2,2,3,3-Tetrafluoropropoxy)phenyl]-4,5-dihydro-5-oxo-1H-1,2,4-triazol-1-yl]propanoic acid (1.0 g) and 2.5 ml of oxalyl chloride were added to 20 ml of dichloromethane, to which dimethylformamide (5 drops) was added dropwise at room temperature. After the reaction solution was stirred at room temperature for 2 hours, the solvent was distilled off under reduced pressure to give 1 g of (2R)-2-[4-[4-(2,2,3,3-tetrafluoropropoxy)phenyl]-4,5-dihydro-5-oxo-1H-1,2,4-triazol-1-yl]propanoyl chloride as a pale yellow oil. This product was used for the next step without purification.

Example 7

To 2.0 g of (2R)-2-[4-[4-(2,2,3,3-tetrafluoropropoxy)phenyl]-4,5-dihydro-5-oxo-1H-1,2,4-triazol-1-yl]propanoic acid was added 20 ml of thionyl chloride and the mixture was stirred at 80° C. for 40 minutes. The reaction solution was concentrated under reduced pressure to give 2.1 g of (2R)-2-[4-[4-(2,2,3,3-tetrafluoropropoxy)phenyl]-4,5-dihydro-5-oxo-1H-1,2,4-triazol-1-yl]propanoyl chloride as a pale yellow oil. This product was used for the next step without purification.

Example 8

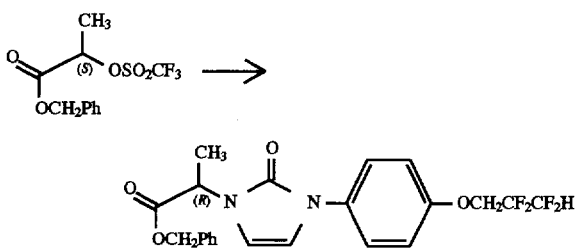

1-[4-(2,2,3,3-Tetrafluoropropoxy)phenyl]-2(1H,3H)-imidazolone (4 g) was dissolved in 30 ml of 1-methyl-2-pyrrolidone, to which 60% sodium hydride in oil (0.55 g) was added. The mixture was vigorously stirred at room temperature for 30 minutes and then added to a solution of 5.2 g of benzyl (2S)-2-trifluoromethanesulfonyloxypropionate (prepared in Example 3) in 80 ml of tetrahydrofuran under nitrogen atmosphere at –40° to –50° C. over the period of 10 minutes. The mixture was stirred at –20° to –40° C. for 50 minutes, followed by addition of 9.6 ml of acetic acid. Then, the reaction solution was diluted with 100 ml of ethyl acetate, washed with 50 ml of water, 1N-hydrochloric acid (50 ml×2) and 50 ml of an aqueous solution of sodium chloride successively, and dried over magnesium sulfate. The solvent was distilled off under reduced pressure and the residue was purified by silica gel chromatography (silica gel: 200 g, eluent; hexane:ethyl acetate=2:3) to give 5.3 g of benzyl (2R)-2-[3-[4-(2,2,3,3-tetrafluoropropoxy)phenyl]-2,3-dihydro-2-oxo-1H-imidazol-1-yl]propionate (yield: 85%) as colorless powdery crystals.

$^1$H-NMR (CDCl$_3$) δ: 1.63 (3H,d,J=7.4 Hz), 4.38 (2H,tt, J=11.8 Hz,1.4 Hz), 5.09 (1H,q,J=7.4 Hz), 5.20 (2H,s), 6.07 (1H, tt,J=53 Hz,4.6 Hz), 6.50 (1H,d,J=3 Hz), 6.57 (1H,d,J=3 Hz), 6.97 (2H,dt,J=9 Hz,2.2 Hz), 7.35 (5H,s) 7.53 (2H,dt, J=9 Hz,2.2 Hz)

mp 75°–76° C.

Elemental analysis for $C_{22}H_{20}F_4N_2O_4$ Calcd: C 58.41, H 4.46, N 6.19 Found: C 58.16, H 4.42, N 6.24

Example 9

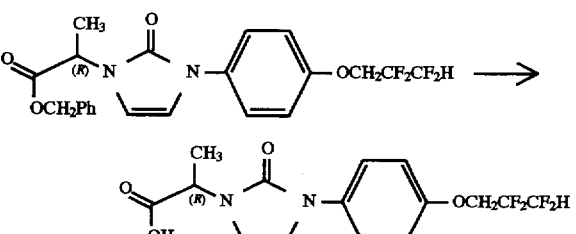

Benzyl (2R)-2-[3-[4-(2,2,3,3-tetrafluoropropoxy)phenyl]-2,3-dihydro-2-oxo-1H-imidazol-1-yl]propionate (5.1 g) was dissolved in 150 ml of ethanol, to which 10% palladium-carbon (0.51 g: containing 50% of water) was added. The mixture was stirred under hydrogen atmosphere at room temperature for 40 minutes.

After the catalyst was removed by filtration, the filtrate was concentrated under reduced pressure. The residue was recrystallized from a mixture of ethanol and diisopropyl ether to give 3.3 g of (2R)-2-[3-[4-(2,2,3,3-tetrafluoropropoxy)phenyl]-2,3-dihydro-2-oxo-1H-imidazol-1-yl]propanoic acid as colorless prisms.

mp 149°–151° C.

$^1$H-NMR (d$_6$-DMSO) δ: 1.54 (3H,d,J=7.2 Hz), 4.55–4.77 (3H, m), 6.69 (1H,tt,J=52 Hz,5.5 Hz), 6.84 (1H,d,J=3 Hz), 7.02 (1H, d,J=3 Hz), 7.13 (2H,d,J=9 Hz), 7.66 (2H,d,J=9 Hz)

Elemental analysis for $C_{15}H_{14}F_4N_2O_4$ Calcd: C 49.73, H 3.90, N 7.73 Found: C 49.64, H 3.93, N 7.72

Example 10

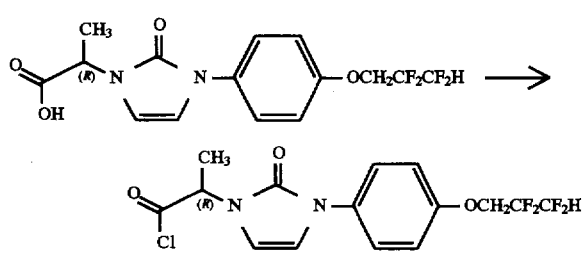

(2R) -2-[3-[4-(2,2,3,3-Tetrafluoropropoxy)phenyl]-2,3-dihydro-2-oxo-1H-imidazol-1-yl]propanoic acid (1.5 g) and 3.8 ml of oxalyl chloride were added to 30 ml of dichloromethane, to which dimethylformamide (7 drops ) was added dropwise at room temperature. After the reaction solution was stirred at room temperature for 2 hours, the solvent was distilled off under reduced pressure to give 1.5 g of (2R)-2-[3-[4-(2,2,3,3-tetrafluoropropoxy)phenyl]-2,3-dihydro-2-oxo-1H-imidazol-1-yl]propanoyl chloride as a pale yellow oil. This product was used for the next step without purification.

Example 11

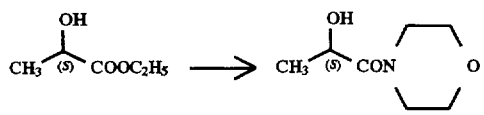

A mixture of 75 g of (S)-ethyl lactate and 164 g of morpholine was heated at 80° C. for 64 hours. The reaction solution was concentrated and purified by silica gel chromatography (eluent; hexane:ethyl acetate=4:1 to ethyl acetate) to give 69.4 g of 4-[(S)-2-hydroxypropionyl]morpholine as a pale yellow oil.

IR (neat): 1635 (C=O) cm$^{-1}$ $^1$H-NMR (CDCl$_3$) δ: 1.34 (3H,d,J=6.6 Hz), 3.43 (2H,t, J=4.8 Hz), 3.55–3.80 (6H,m), 3.79 (1H,d,J=7.4 Hz), 4.38–4.53 (1H,m)

Example 12

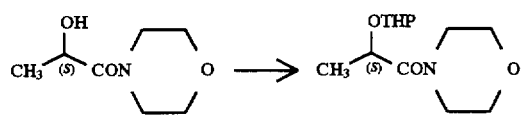

To a solution of 69.4 g of 4-[(S)-2-hydroxypropionyl]-morpholine in 300 ml of dichloromethane was added 0.82 g of p-toluenesulfonic acid monohydrate, to which 40.3 g of 3,4-dihydro-2H-pyran was added dropwise with ice cooling. The reaction solution was stirred at 0° C. for 30 minutes and washed with an aqueous solution of 5% sodium bicarbonate. The organic layer was dried over magnesium sulfate and concentrated. The residue was purified by silica gel chromatography (eluent; hexane:ethyl acetate=8:1 to ethyl acetate) to give 89.1 g of 4-[(2S)-2-(3,4,5,6-tetrahydro-2H-pyran-2-yloxy)propionyl]morpholine as a pale yellow oil.

IR (neat): 1662, 1650 cm$^{-1}$ $^1$H-NMR (CDCl$_3$) δ: 1.39, 1.44 (3H,d each,J=6.8 Hz), 1.40–1.95 (6H,m), 3.40–3.95 (10H,m), 4.48–4.75 (2H,m)

Example 13

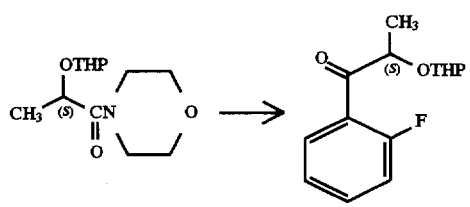

1-Bromo-2-fluorobenzene (15 g) and 40 g of 4-[(2S)-2-(3,4,5,6-tetrahydro-2H-pyran-2-yloxy)propionyl] morpholine was dissolved in 200 ml of tetrahydrofuran, to which 44 g of magnesium turnings was added, and the mixture was vigorously stirred. The reaction vessel was cooled when a temperature of the reaction solution was raised to 35° C., and 16.7 g of 1-bromo-2-fluorobenzene was added dropwise to the reaction solution at 35° to 37° C. over the period of 10 minutes. After stirring at 30° to 35° C. for 2 hours, the reaction solution was ice-cooled, to which 100 ml of a saturated aqueous solution of ammonium chloride and 100 ml of water were added. The mixture was extracted with ethyl acetate (200 ml×2, 100 ml). Then, the extract was washed with water and an aqueous solution of sodium chloride successively, and dried over magnesium sulfate. The solvent was distilled off under reduced pressure and the residue was purified by silica gel chromatography (eluent; hexane:ethyl acetate=10:1 to 5:1) to give 22.4 g of (2S)-2'-fluoro-2-(3,4,5,6-tetrahydro-2H-pyran-2-yloxy) propiophenone as a pale yellow oil.

IR (neat): 2942, 1697, 1608, 1558, 1540, 1456 cm$^{-1}$ $^1$H-NMR (CDCl$_3$) δ: 1.40–2.00 (9H,m), 3.29–3.60 (1H, m), 3.65–3.98 (1H,m), 4.65–4.88 (1H,m) 4.92, 5.15 (1H,q each, J=7 Hz), 7.08–7.29 (2H,m), 7.43–7.60 (1H,m), 7.78–7.90 (1H,m)

Example 14

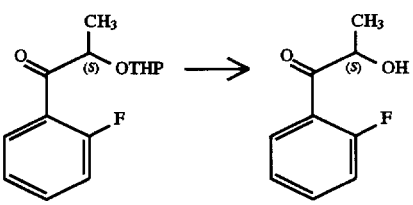

(2S)-2'-Fluoro-2-(3,4,5,6-tetrahydro-2H-pyran-2-yloxy) propiophenone (25 g) was dissolved in 200 ml of ethanol, to which 1.28 g of pyridinium p-toluenesulfonate was added. The mixture was stirred at 55° C. for 2.5 hours and then concentrated. The residue was purified by silica gel chromatography (eluent; hexane:ethyl acetate=9:1 to 5:1) to give 16.4 g of (2S)-2'-fluoro-2-hydroxypropiophenone as a colorless oil.

IR (neat): 1690 (C=O) cm$^{-1}$ $^1$H-NMR (CDCl$_3$) δ: 1.41 (3H,dd,J=7 Hz,J=1.4 Hz), 3.78 (1H, d,J=6 Hz), 4.98–5.15 (1H,m), 7.12–7.36 (2H,m), 7.54–7.68 (1H, m), 7.90–8.00 (1H,m)

The optical purity of this product was measured by HPLC method [column: Chiral Cell OB (4.6 mmϕ×25 cm, manufactured by Daicel Chemical Industries, Ltd.), mobile phase; hexane:2-propanol=4:1, flow rate: 1 ml/min], by which enantiomer excess (ee) of the product was determined to be 97.9%.

Example 15

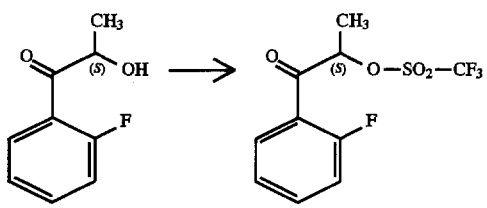

(2S)-2'-Fluoro-2-hydroxypropiophenone (3.36 g, synthesized with the method described in Example 14) was dissolved in 30 ml of dichloromethane, to which 4.18 ml of diisopropylethylamine was added at -60° C. under nitrogen atmosphere. Then, to the mixture was added dropwise 4.03 ml of trifluoromethanesulfonic anhydride over the period of 2 minutes. The reaction temperature was gradually raised to -25° C., and then the reaction solution was stirred for 30 minutes and purified by silica gel chromatography (silica gel: 60 g, eluent; dichloromethane:hexane=1:1) to give 5.30 g of (2S)-2'-fluoro-2-fluoromethanesulfonyl-oxypropiophenone as a pale yellow oil.

$^1$H-NMR (CDCl$_3$) δ: 1.73 (3H,dd,J=7 Hz,J=1.6 Hz), 6.49 (1H, q,J=7 Hz), 7.15–7.38 (2H,m), 7.58–7.72 (1H,m), 7.97 (1H,dt, J=1,8 Hz,J=7.6 Hz)

Example 16

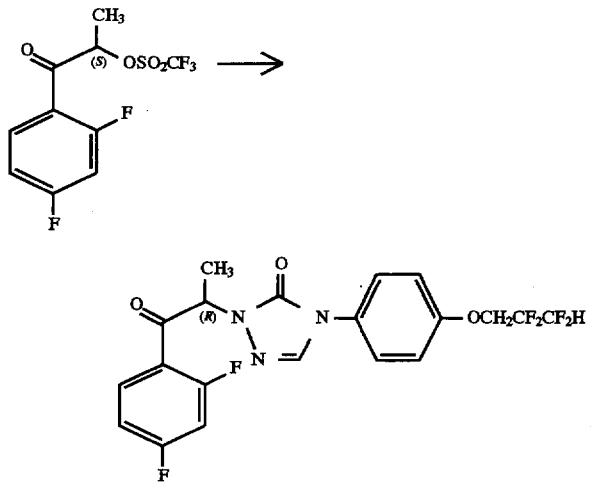

4-[4-(2,2,3,3-Tetrafluoropropoxy)phenyl]-3(2H,4H)-1,2,4-triazolone (6.12 g) was dissolved in 60 ml of 1-methyl-2-pyrrolidone, to which 60% of sodium hydride in oil (0.80 g) was added, and the mixture was stirred at room temperature for 3 hours. The reaction solution was ice-cooled and added dropwise under nitrogen atmosphere over the period of 25 minutes to a solution of 7.32 g of (2S)-2',4'-difluoro-2-trifluoromethanesulfonyloxypropiophenone in 180 ml of tetrahydrofuran which was cooled to -50° C. Then, the reaction temperature was raised to -30° C. over the period of 10 minutes. After stirring for 30 minutes, the reaction solution was diluted with 10 ml of acetic acid and 500 ml of ethyl acetate, washed with water (300 ml×2), 0.5N-hydrochloric acid (400 ml×2) and 300 ml of a saturated aqueous solution of sodium chloride successively, and dried over magnesium sulfate. The solvent was distilled off under reduced pressure. The residue was purified by silica gel chromatography (silica gel: 250 g, eluent; hexane:ethyl acetate:acetic acid=3:1:0.04), and dissolved in 12 ml of diisopropyl ether. The solution was allowed to stand for 1 hour with ice cooling. The deposited insoluble substance was removed by filtration and the solution was concentrated under reduced pressure to give 5.36 g of 2-[(1R)-2-(2,4-difluorophenyl)-2-oxo-1-methylethyl]-4-[4-(2,2,3,3-tetrafluoropropoxy)phenyl]-3(2H,4H)-1,2,4-triazolone as a pale yellow viscous substance.

This product was analyzed by HPLC (mobile phase; hexane:isopropyl alcohol=1:1) using chiral column [Chiral PakAD (0.46 cmϕ×25 cm), manufactured by Daicel Chemical Industries, LTD.], by which enantiomer excess (ee) of the product was determined to be 98%.

$^1$H-NMR (CDCl$_3$) δ: 1.75 (3H,d,J=7 Hz), 4.38 (2H,tt, J=11.8 Hz,1.4 Hz), 5.70 (1H,q,J=7 Hz), 6.06 (1H,tt,J=53 Hz, 4.8 Hz), 6.85–7.05 (2H,m), 7.02 (2H,dt,J=9 Hz,2.4 Hz), 7.49 (2H,dt,J=9 Hz,2.4 Hz), 7.68 (1H,s), 7.94 (1H,dt,J=6.4 Hz,8.6 Hz)

$[α]_D^{23}$+69.8° (c=1.2, in methanol)

Elemental analysis for $C_{20}H_{15}F_6N_3O_3$ Calcd: C 52.30, H 3.29, N 9.15 Found: C 52.41, H 3.48, N 8.89

Example 17

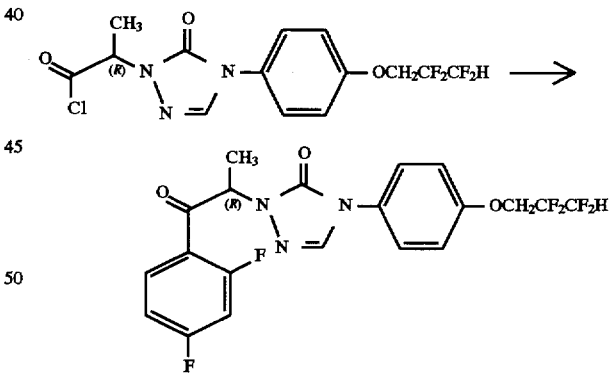

(2R)-2-[4-[4-(2,2,3,3-Tetrafluoropropoxy)phenyl]-4,5-dihydro-5-oxo-1H-1,2,4-triazol-1-yl]propanoyl chloride (1 g) was dissolved in 20 ml of dichloromethane, to which 2.5 ml of 1,3-difluorobenzene and 1.50 g of anhydrous aluminium chloride in a powdery form were added. The mixture was refluxed with heating for eight hours. After cooling, the reaction solution was poured into 50 ml of ice water and extracted from a mixture of 100 ml of ethyl acetate and 50 ml of diisopropyl ether. The extract was washed with 30 ml of 1N-hydrochloric acid and 30 ml of a saturated aqueous solution of sodium chloride successively, and dried over magnesium sulfate. The solvent was distilled off under reduced pressure. The residue was purified by silica gel chromatography (silica gel: 60 g, eluent; hexane:ethyl acetate:acetic acid=2:1:0.03) to give 0.77 g of 2-[(1R)-2-(2,4-difluorophenyl)-2-oxo-1-methylethyl]-4-[4-(2,2,3,3-tetrafluoropropoxy)phenyl]-3(2H,4H)-1,2,4 -triazolone (yield: 61%) as a pale yellow oil.

The enantiomer excess (ee) of this product was determined to be 93% by HPLC using Chiral Pak AD.

$^1$H-NMR (CDCl$_3$) δ: 1.75 (3H,d,J=7 Hz), 4.38 (2H,tt, J=11.8 Hz,J=1.6 Hz), 5.70 (1H,q,J=7 Hz), 6.06 (1H,tt,J=53 Hz, J=4.6 Hz), 6.85–7.05 (2H,m), 7.02 (2H,dt,J=9 Hz,J=2.4 Hz), 7.49 (2H,dt,J=9 Hz,J=2.4 Hz), 7.68 (1H, s), 7.94 (1H,dt, J=6.4 Hz,J=8.6 Hz)

Example 18

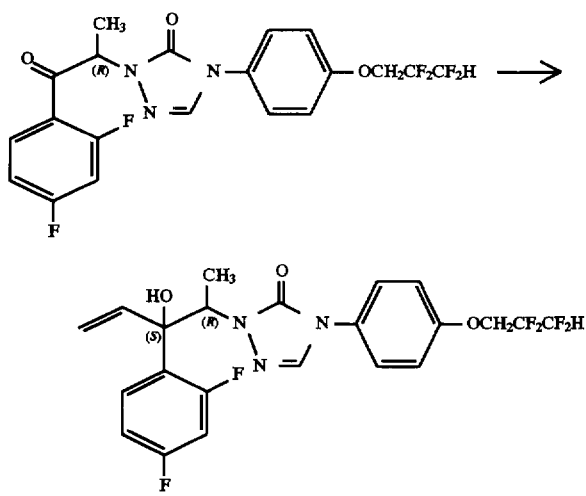

A solution of 2-[(1R)-2-(2,4-difluorophenyl)-2-oxo-1-methylethyl]-4-[4-(2,2,3,3-tetrafluoropropoxy)phenyl]-3(2H,4H)-1,2,4-triazolone (1.16 g: 98% ee) in 20 ml of tetrahydrofuran was cooled to –60° C. and 5 ml of a solution of 1M vinyl magnesium bromide in tetrahydrofuran was added thereto dropwise over the period of 13 minutes. The reaction solution was stirred at –30° C. for 2 hours, to which 5 ml of a saturated aqueous solution of ammonium chloride was added. The reaction mixture was extracted with a mixture of 60 ml of ethyl acetate and 30 ml of diisopropyl ether. The extract was washed with 20 ml of water and 20 ml of an aqueous solution of sodium chloride successively, and dried over magnesium sulfate. The solvent was distilled off under reduced pressure and the residue was purified by silica gel chromatography (silica gel: 70 g, eluent; hexane:ethyl acetate=3:1 to 2:1). The desired fraction was concentrated and the residue was recrystallized from a mixture of diisopropyl ether and hexane to give 0.81 g of 2-[(1R,2S)-2-(2,4-difluorophenyl)-2-hydroxy-1-methyl-3-propenyl]4-[4-(2,2,3,3-tetrafluoropropoxy)phenyl]-3(2H,4H)-1,2,4-triazolone as colorless needles.

mp 104°–106° C.

$^1$H-NMR (CDCl$_3$) δ: 1.26 (3H,d,J=7 Hz), 4.39 (2H,tt, J=11.8 Hz,J=1.4 Hz), 4.93 (1H,s), 5.03 (1H,d,J=9.5 Hz), 5.11 (1H,q,J=7 Hz), 5.43 (1H,dt,J=17.2 Hz,J=1.6 Hz), 6.06 (1H,tt, J=53 Hz,J=4.8 Hz), 6.40–6.58 (1H,m), 6.75–6.96 (2H,m), 7.04 (2H,dt,J=9 Hz,J=2.8 Hz), 7.48 (2H,dt,J=9 Hz,J=2.8 Hz), 7.66 (1H, s), 7.75–7.88 (1H,m)

[α]$_D^{23}$ –26.0° (c=0.54, in methanol)

Elemental analysis for C$_{22}$H$_{19}$F$_6$N$_3$O$_3$ Calcd: C 54.21, H 3.93, N 8.62 Found: C 54.24, H 3.91, N 8.47

Example 19

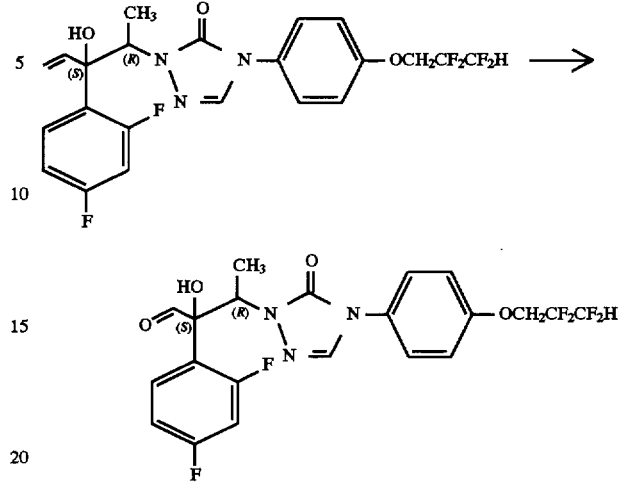

2-[(1R,2S)-2-(2,4-Difluorophenyl)-2-hydroxy-1-methyl-3-propenyl]-4-[4-(2,2,3,3-tetrafluoropropoxy)phenyl]-3(2H,4H)-1,2,4-triazolone (0.60 g) was dissolved in 20 ml of dichloromethane and ozone was bubbled through the solution at –60° C. over the period of 20 minutes. The bubbling ozone was stopped when the reaction solution turned pale purple. Nitrogen gas was bubbled through the reaction solution for 10 minutes, to which dimethylsulfide (0.6 ml) was added. The mixture was stirred at room temperature until the temperature of the reaction solution was raised to 0° C. The reaction solution was diluted with 100 ml of ethyl acetate, washed with 10 ml of water and 10 ml of an aqueous solution of sodium chloride successively, and dried over magnesium sulfate. After the solvent was distilled off under reduced pressure, the residue was recrystallized from a mixture of diisopropyl ether and hexane to give 0.46 g of 2-[(1R,2S)-2-(2,4-difluorophenyl)-2-formyl-2-hydroxy-1-methylethyl]-4-[4-(2,2,3,3-tetrafluoropropoxy)phenyl]-3(2H,4H)-1,2,4-triazolone as colorless prisms.

mp 134°–136° C.

$^1$H-NMR (CDCl$_3$) δ: 1.35 (3H,d,J=7 Hz), 4.38 (2H,tt, J=11.8 Hz,J=1.4 Hz), 4.81 (1H,s), 5.42 (1H,q,J=7 Hz), 6.06 (1H, tt,J=53 Hz,J=4.8 Hz), 6.84–7.10 (2H,m), 7.03 (2H,dt, J=9 Hz, J=2.2 Hz), 7.47 (2H,dt,J=9 Hz,J=2.2 Hz), 7.66 (1H,s), 7.73–7.85 (1H,m), 9.97 (1H,dd,J=3.2 Hz,J=1 Hz)

Elemental analysis for C$_{21}$H$_{17}$F$_6$N$_3$O$_4$ Calcd: C 51.54, H 3.50, N 8.59 Found: C 51.39, H 3.50, N 8.42

Example 20

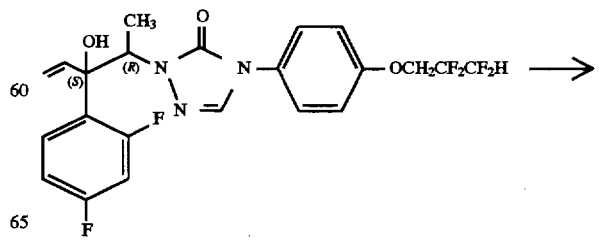

-continued

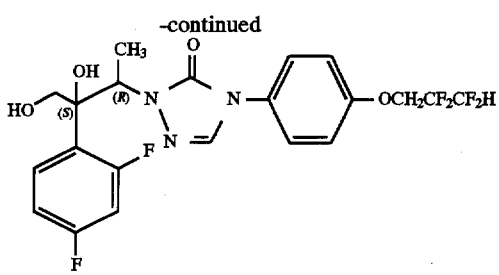

2-[(1R,2S)-2-(2,4-Difluorophenyl)-2-hydroxy-1-methyl-3-propenyl]-4-[4-(2,2,3,3-tetrafluoropropoxy)phenyl]-3 (2H,4H)-1,2,4-triazolone (244 mg) was dissolved in 5.7 ml of methanol, to which 2 ml of an aqueous solution of 321 mg of sodium metaperiodate and 3 mg of osmium tetroxide. The mixture was stirred at room temperature for 18 hours.

To the reaction solution was added 50 ml of ethyl acetate to fractionate. Then, the organic layer was washed with 10 ml of water and 10 ml of an aqueous solution of sodium chloride successively and dried over magnesium sulfate. After the solvent was distilled off under reduced pressure, the residue was dissolved in 8 ml of methanol, to which 20 mg of sodium borohydride was added. Then, the mixture was stirred at room temperature for 30 minutes.

The reaction solution was diluted with 50 ml of ethyl acetate, washed with 10 ml of water and 10 ml of a saturated aqueous solution of sodium chloride successively, and dried over magnesium sulfate. After the solvent was distilled off under reduced pressure, the residue was purified by silica gel chromatography (silica gel: 15 g, eluent; hexane:ethyl acetate=2:1 to 1:1) to give 29 mg of 2-[(1R,2S)-2-(2,4-difluorophenyl)-2,3-dihydroxy-1-methylpropyl]-4-[4-(2,2,3,3-tetrafluoropropoxy)phenyl]-3(2H,4H)-1,2,4-triazolone as a colorless powder. SIMS 492(MH⁺)

Example 21

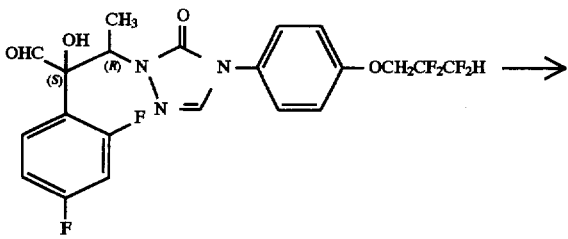

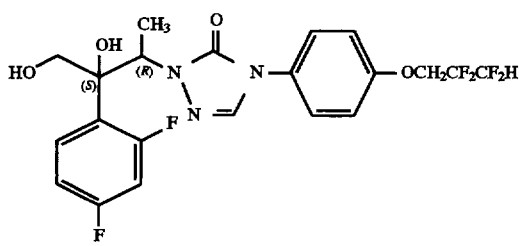

2-[(1R,2S)-2-(2,4-Difluorophenyl)-2-formyl-2-hydroxy-1-methylethyl]-4-[4-(2,2,3,3-tetrafluoropropoxy)phenyl]-3 (2H,4H)-1,2,4-triazolone (300 mg) was dissolved in 9 ml of methanol, to which 74 mg of sodium borohydride was added at 0° C. The mixture was stirred with ice cooling for 30 minutes. To the reaction solution was added 1 ml of 1N-hydrochloric acid and 50 ml of ethyl acetate, and then the organic layer was washed with 10 ml of water and 10 ml of an aqueous solution of sodium chloride successively. The organic layer was dried over magnesium sulfate. The solvent was distilled off under reduced pressure. The residue was purified by silica gel chromatography (eluent; hexane:ethyl acetate=1:1) to give 165 mg of 2-[(1R,2S)-2-(2,4-difluorophenyl)-2,3-dihydroxy-1-methylpropyl]-4-[4-(2,2,3,3-tetrafluoro-propoxy)phenyl]-3(2H,4H)-1,2,4-triazolone as colorless prisms.

The enantiomer excess (ee) of this product was determined to be >99% by HPLC using Chiral Pak AD.

mp 144°–145° C.

Elemental analysis for $C_{21}H_{19}F_6N_3O_4$ Calcd: C 51.33, H 3.90, N 8.55 Found: C 51.30, H 3.82, N 8.60

Example 22

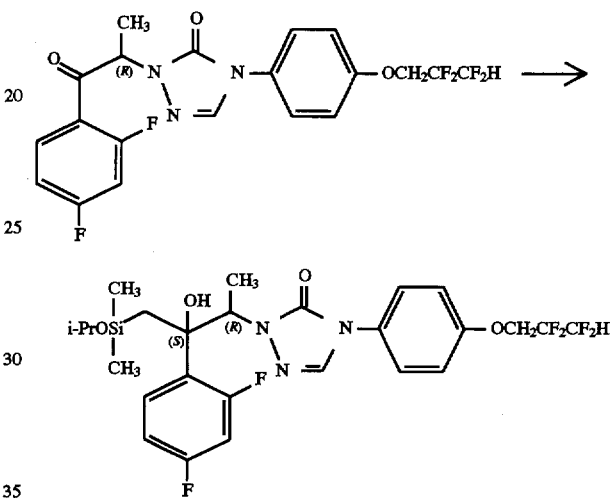

Chloromethylisopropoxydimethyl silane (18.1 g) and 2.65 g of magnesium (for Grignard reaction) were added to 100 ml of tetrahydrofuran and the mixture was heated to 45° to 50° C. After adding magnesium tips which were activated with methyl iodide, the mixture was stirred at 45° to 50° C. for 3 hours.

The solution containing the Grignard reagent thus obtained was ice-cooled, to which a solution of 2-[(1R)-2-(2,4-difluorophenyl)-2-oxo-1-methylethyl]-4-[4-(2,2,3,3-tetrafluoropropoxy)phenyl]-3(2H,4H)-1,2,4-triazolone (10.5 g, 97% ee) in 50 ml of tetrahydrofuran was added dropwise over the period of 20 minutes. The mixture was stirred at room temperature for 20 minutes and then ice-cooled. To the mixture was added 50 ml of a cooled saturated aqueous solution of ammonium chloride and 50 ml of cooled water. The mixture was extracted with 300 ml of ethyl acetate and 150 ml of diisopropyl ether. The extract was washed with an aqueous solution of sodium chloride, dried over magnesium sulfate and concentrated under reduced pressure. The residue was purified by silica gel chromatography (silica gel: 200 g, eluent; hexane:ethyl acetate=2:1). The desired fraction was concentrated and the residue was recrystallized from a mixture of 50 ml of diisopropyl ether and 100 ml of hexane to give 11.03 g of 2-[(1R,2S)-2-(2,4-difluorophenyl)-2-hydroxy-3-(isopropoxydimethylsilyl)-1-methylpropyl]-4-[4-(2,2,3,3-tetrafluoropropoxy)phenyl]-3(2H,4H)-1,2,4-triazolone (yield: 82%) as colorless needles.

mp 125°–126° C.

$[\alpha]_D^{23}$+2.8° (c=1.0, in methanol)

Elemental analysis for $C_{26}H_{31}F_6N_3O_4Si$ Calcd: C 52.78, H 5.28, N 7.10 Found: C 52.82, H 5.30, N 6.96

The enantiomer excess (ee) of this product was determined to be 99.3% by HPLC using Chiral Pak AD.

Example 23

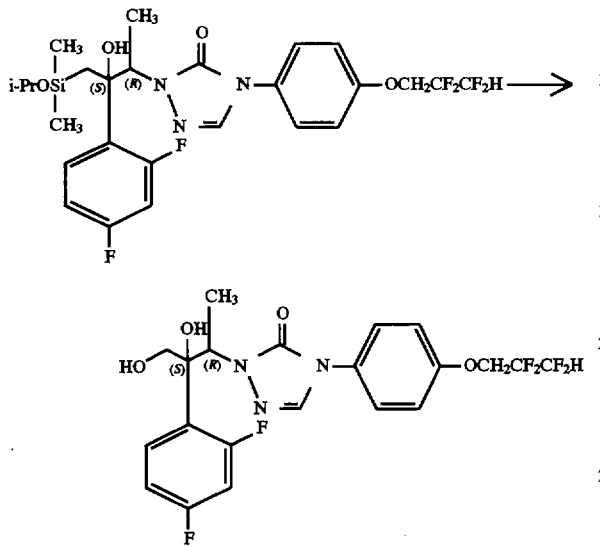

2-[(1R,2S)-2-(2,4-Difluorophenyl)-2-hydroxy-3-(isopropoxydimethylsilyl)-1-methylpropyl]-4-[4-(2,2,3,3-tetrafluoropropoxy)phenyl]-3(2H,4H)-1,2,4-triazolone (11 g) was dissolved in a mixture of methanol and tetrahydrofuran (1:1, 90 ml), to which 19.2 ml of 30% aqueous hydrogen peroxide and 1.57 g of sodium hydrogencarbonate were added. Then, the mixture was heated at 70° to 80° C. for 90 minutes. The reaction solution was cooled and extracted with a mixture of 500 ml of ethyl acetate and 100 ml of diisopropyl ether. The extract was washed with 100 ml of water, an aqueous solution of $Na_2S_2O_3$ (50 ml×2) and 50 ml of an aqueous solution of sodium chloride successively, and dried over magnesium sulfate. After the solvent was distilled off under reduced pressure, the residue was recrystallized from 50 ml of diisopropyl ether to give 8.27 g of 2-[(1R,2S)-2-(2,4-difluorophenyl)-2,3-dihydroxy-1-methylpropyl]-4-[4 -(2,2,3,3-tetrafluoropropoxy)phenyl]-3 (2H,4H)-1,2,4-triazolone as colorless prisms. The mother liquor of recrystallization was submitted to silica gel chromatography (silica gel: 40 g, eluent; hexane:ethyl acetate= 1:1). The resultant was recrystallized from diisopropyl ether to give 0.33 g of the above compound (total yield: 93.7%).

mp 144°–145° C.

$[\alpha]_D^{23}$ –6.3° (c=1.0, in methanol)

Elemental analysis for $C_{21}H_{19}F_6N_3O_4$ Calcd: C 51.33, H 3.90, N 8.55 Found: C 51.15, H 3.76, N 8.52

$^1$H-NMR (CDCl$_3$) δ: 1.29 (3H,d,J=7 Hz), 2.09–2.21 (1H, m), 3.82–4.00 (2H,m), 4.40 (2H,tt,J=11.8 Hz,J=1.4 Hz), 4.80 (1H, s), 5.04 (1H,q,J=7 Hz), 6.06 (1H,tt,J=53 Hz,J=4.6 Hz), 6.75–7.00 (2H,m), 7.05 (2H,dt,J=9 Hz,J=2.2 Hz), 7.50 (2H,dt,J=9 Hz, J=2.2 Hz), 7.71 (1H,s), 7.73–7.84 (1H,m)

Example 24

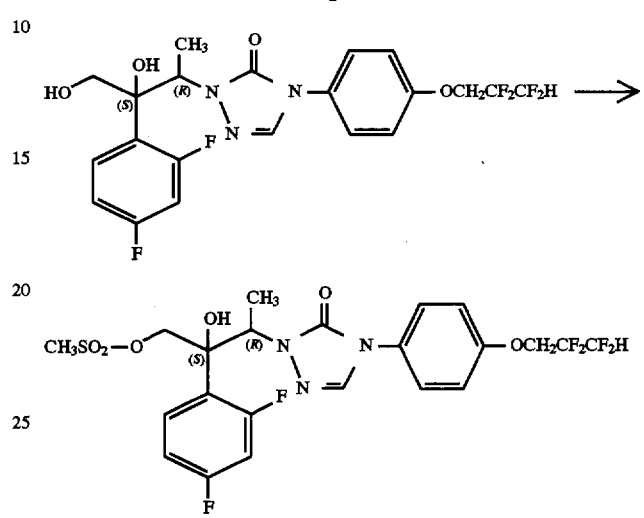

2-[(1R,2S)-2-(2,4-Difluorophenyl)-2,3-dihydroxy-1-methylpropyl]-4-[4-(2,2,3,3-tetrafluoropropoxy)phenyl]-3 (2H,4H)-1,2,4-triazolone (8.26 g) was dissolved in 100 ml of ethyl acetate, to which 2.89 g of methanesulfonyl chloride and 2.54 g of triethylamine were added dropwise with ice cooling. After stirring at 0° C. for 30 minutes, the solution was washed with water (20 ml×2) and 20 ml of an aqueous solution of sodium chloride successively. The organic layer was dried over magnesium sulfate. The solvent was distilled off under reduced pressure to give 10 g of 2-[(1R,2S)-2-(2, 4-difluorophenyl)-2-hydroxy-3-methanesulfonyloxy-1-methylpropyl]-4-[4-(2,2,3,3-tetrafluoropropoxy)phenyl]-3 (2H,4H)-1,2,4-triazolone as a colorless oil.

$^1$H-NMR (CDCl$_3$) δ: 1.27 (3H,d,J=7 Hz), 2.91 (3H,s), 4.40 (2H,tt,J=11.8 Hz,J=1.6 Hz), 4.49–4.59 (2H,m), 5.05 (1H,q, J=7 Hz), 5.34 (1H,s), 6.06 (1H,tt,J=53 Hz,J=4.8 Hz), 6.80–7.05 (2H,m), 7.06 (2H,d,J=9.2 Hz), 7.53 (2H,d,J=9,2 Hz), 7.72 (1H, s), 7.78–7.92 (1H,m)

Example 25

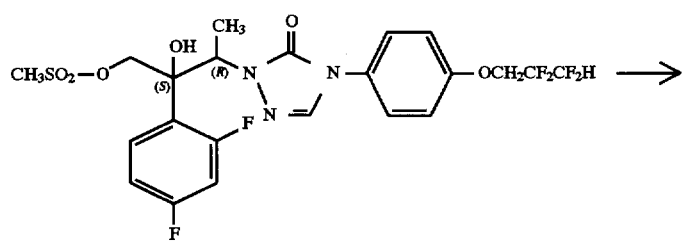

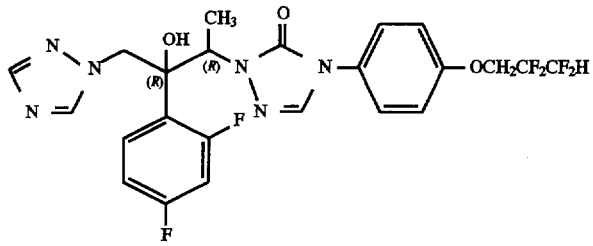

2-[(1R,2S)-2-(2,4-Difluorophenyl)-2-hydroxy-3-methanesulfonyloxy-1-methylpropyl]-4-[4-(2,2,3,3-tetrafluoropropoxy)phenyl]-3(2H,4H)-1,2,4-triazolone (10 g) was dissolved in 180 ml of dimethylformamide, to which 5.7 g of 1H-1,2,4-triazole and 23.2 g of potassium carbonate were added. The mixture was heated at 90° C. for 5 hours. The reaction solution was concentrated under reduced pressure to ca. 100 ml and diluted with a mixture of 400 ml of ethyl acetate and 200 ml of diisopropyl ether. The mixture was washed with 100 ml of water, 1N-hydrochloric acid (100 ml×2) and 100 ml of an aqueous solution of sodium chloride successively. The organic layer was dried over magnesium sulfate. After the solvent was distilled off under reduced pressure, the residue was purified by silica gel chromatography (silica gel: 70 g, eluent; hexane:ethyl acetate=3:4 to ethyl acetate). The desired fraction was concentrated and the residue was recrystallized from a mixture of 10 ml of ethyl acetate and 80 ml of diisopropyl ether to give 7.3 g of 2-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl]-3(2H,4H)-1,2,4-triazolone (yield: 80%) as a colorless powdery crystals.

The enantiomer excess (ee) of this product was determined to be >99% by HPLC using Chiral Pak AD.

Elemental analysis for $C_{23}F_{20}F_6N_6O_3$ Calcd: C 50.93, H 3.72, N 15.49 Found: C 50.93, H 3.63, N 15.61

$^1$H-NMR (CDCl$_3$) δ: 1.30 (3H,d,J=7 Hz), 4.36 (1H,d, J=15 Hz), 4.40 (2H,tt,J=11.8 Hz,J=1.4 Hz), 5.01 (1H,d,J=15 Hz), 5.08 (1H,q,J=7 Hz), 5.47 (1H,s), 6.06 (1H,tt,J=53 Hz,J=4.6 Hz), 6.75–6.88 (2H,m), 7.07 (2H,dt,J=9 Hz,J=2.2 Hz), 7.53 (2H,dt, J=9 Hz,J=2.2 Hz), 7.48–7.64 (1H,m), 7.68 (1H,s), 7.74 (1H,s), 7.94 (1H, s)

[α]$_D^{20}$–22.3° (c=1.01, in methanol)

Example 26

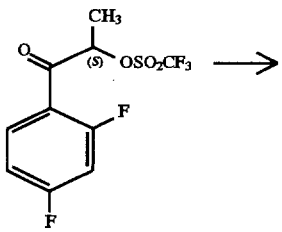

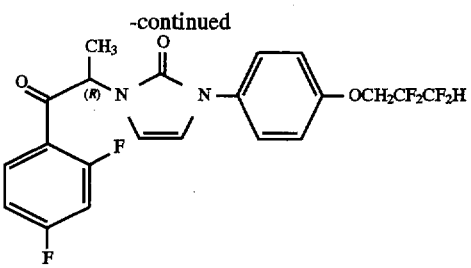

1-[4-(2,2,3,3-Tetrafluoropropoxy)phenyl]-2(1H,3H)-imidazolone (6.58 g) was dissolved in 45 ml of 1-methyl-2-pyrrolidone, to which 0.86 g of 60% sodium hydride in oil was added. The mixture was stirred at room temperature for 15 hours. The ice-cooled mixture was added dropwise under nitrogen atmosphere over the period of 15 minutes to a solution of 7.98 g of (2S)-2',4'-difluoro-2-trifluoromethanesulfonyloxypropiophenone in 150 ml of tetrahydrofuran which was cooled to –40° C. After the reaction temperature was raised to –20° C. over the period of 20 minutes, the reaction solution was stirred for 10 minutes. The reaction solution was diluted with 16 ml of acetic acid and 200 ml of ethyl acetate, washed with water (100 ml×2), 0.5N-hydrochloric acid (100 ml×2) and 100 ml of a saturated aqueous solution of sodium chloride successively, and dried over anhydrous magnesium chloride. After the solvent was distilled off under reduced pressure, the residue was purified by silica gel chromatography (silica gel: 1 kg, eluent; hexane:ethyl acetate:acetic acid=2:1:0.08) and recrystallized from 20 ml of diisopropyl ether to give 4 g of 1-[(1R)-2-(2,4-difluorophenyl)-2-oxo-1-methylethyl]-3-[4-(2,2,3,3-tetrafluoropropoxy)phenyl]-2(1H,3H)-imidazolone as colorless powdery crystals.

The enantiomer excess (ee) of this product was determined to be 99% by HPLC using Chiral Pak AD.

$^1$H-NMR (CDCl$_3$) δ: 1.62 (3H,d,J=7 Hz), 4.35 (2H,tt, J=11.8 Hz,1.4 Hz), 5.74 (1H,q,J=7 Hz), 6.07 (1H,tt,J=53 Hz, 4.8 Hz), 6.56 (2H,s), 6.57–7.05 (2H,m), 6.96 (2H,dt,J=9 Hz, 2,4 Hz), 7.52 (2H,dt,J=9 Hz,2.4 Hz), 7.94–8.05 (1H,m)

[α]$_D^{20}$=+10.5° (c=1.0, in methanol)

Example 27

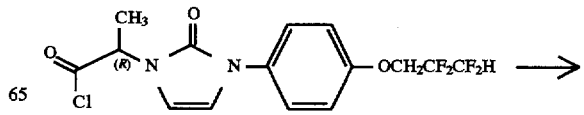

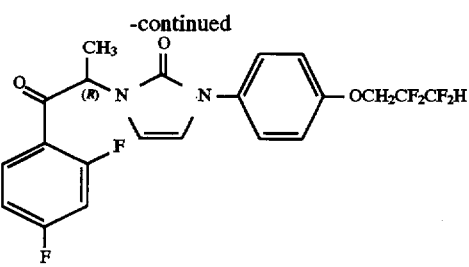

(2R)-2-[3-[4-(2,2,3,3-Tetrafluoropropoxy)phenyl]-2,3-dihydro-2-oxo-1H-imidazol-1-yl]propanoyl chloride (1.5 g) was dissolved in 30 ml of dichloromethane, to which 3.8 ml of 1,3-difluorobenzene and 2.3 g of anhydrous aluminum chloride (powder) were added. The mixture was refluxed with heating for 5 hours. The reaction solution was cooled, poured into 100 ml of ice water and extracted with 100 ml of ethyl acetate. The extract was washed with 50 ml of 1N-hydrochloric acid and 50 ml of a saturated aqueous solution of sodium chloride successively, and dried over magnesium sulfate. The solvent was distilled off under reduced pressure. The residue was purified by silica gel chromatography (silica gel: 50 g, eluent; hexane:ethyl acetate:acetic acid=2:1:0.03) and crystallized from 10 ml of diisopropyl ether to give 0.25 g of 1-[(1R)-2-(2,4-difluorophenyl)-2-oxo-1-methylethyl]-3-[4-(2,2,3,3-tetrafluoropropoxy)phenyl]-2(1H,3H)-imidazolone as colorless powdery crystals.

$^1$H-NMR (CDCl$_3$) δ: 1.63 (3H,d,J=7 Hz), 4.35 (2H,tt, J=11.8 Hz,1.4 Hz), 5.74 (1H,q,J=7 Hz), 6.09 (1H,tt,J=53 Hz, 4.8 Hz), 6.56 (2H,s), 6.56–7.04 (2H,m), 6.96 (2H,dt,J=9 Hz, 2.4 Hz), 7.53 (2H,dt,J=9 Hz,2.4 Hz), 7.94–8.06 (1H,m)

Elemental analysis for C$_{21}$H$_{16}$F$_6$N$_2$O$_3$ Calcd: C 55.03, H 3.52, N 6.11 Found: C 54.89, H 3.59, N 6.04

Example 28

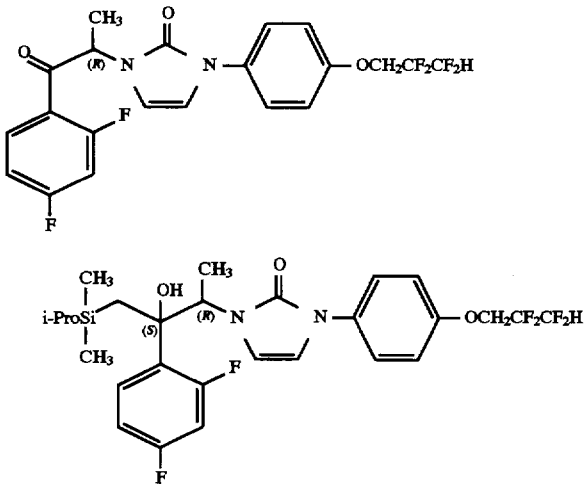

Chloromethylisopropoxydimethyl silane (6.94 g) and 1.02 g of magnesium (for Grignard reaction) were added to 50 ml of tetrahydrofuran and the mixture was heated to 50° C. After adding magnesium tips which were activated with methyl iodide, the mixture was stirred at 50° C. for 3 hours, The solution containing the Grignard reagent thus obtained was ice-cooled and a solution of 3.9 g of 1-[(1R)-2-(2,4-difluorophenyl)-2-oxo-1-methylethyl]-3-[4-(2,2,3,3-tetrafluoropropoxy)phenyl]-2(1H,3H)-imidazolone in 30 ml of tetrahydrofuran was added thereto dropwise over the period of 5 minutes. The mixture was stirred at room temperature for 15 minutes. The reaction solution was ice-cooled, and 25 ml of a cooled saturated aqueous solution of ammonium chloride and 50 ml of cooled water were added thereto. The mixture was extracted with 200 ml of ethyl acetate. The extract was washed with an aqueous solution of sodium chloride, dried over magnesium sulfate and concentrated under reduced pressure. The residue was purified by silica gel chromatography (silica gel: 150 g, eluent; hexane:ethyl acetate=3:1). The desired fraction was concentrated and the residue was recrystallized from a mixture of 10 ml of diisopropyl ether and 20 ml of hexane to give 1.42 g of 1-[(1R,2S)-2-(2,4-difluorophenyl)-2-hydroxy-3-(isopropoxydimethylsilyl)-1-methylpropyl]-3-[4-(2,2,3,3-tetrafluoropropoxy)phenyl]-2(1H,3H)-imidazolone as colorless needles.

Elemental analysis for C$_{27}$H$_{32}$F$_6$N$_2$O$_4$Si Calcd: C 54.91, H 5.46, N 4.74 Found: C 54.65, H 5.32, N 4.74

Example 29

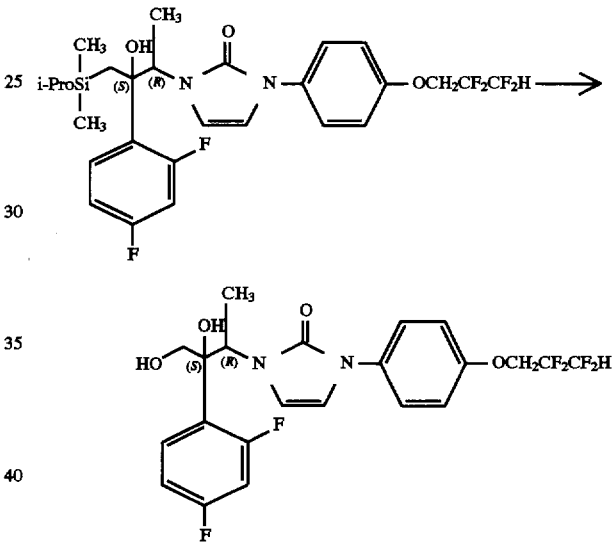

1-[(1R,2S)-2-(2,4-Difluorophenyl)-2-hydroxy-3-(isopropoxydimethylsilyl)-1-methylpropyl]-3-[4-(2,2,3,3-tetrafluoropropoxy)phenyl]-2(1H,3H)-imidazolone (1.8 g) was dissolved in a mixture of methanol and tetrahydrofuran (1:1, 20 ml), to which 3.21 ml of 30% aqueous hydrogen peroxide and 0.262 g of sodium hydrogencarbonate were added. The mixture was heated at 70° to 80° C. for 90 minutes, cooled and extracted with 100 ml of ethyl acetate. The extract was washed with 50 ml of water, an aqueous solution of Na$_2$S$_2$O$_3$ (50 ml×2) and 50 ml of an aqueous solution of sodium chloride successively, and dried over magnesium sulfate. After the solvent was distilled off under reduced pressure, the residue was purified by silica gel chromatography (silica gel: 50 g, eluent; hexane:ethyl acetate=2:3) and recrystallized from diisopropyl ether to give 1.32 g of 1-[(1R,2S)-2-(2,4-difluorophenyl)-2,3-dihydroxy-1-methylpropyl]-3-[4-(2,2,3,3-tetrafluoropropoxy)phenyl]-2(1H,3H)-imidazolone (yield: 88%) as colorless prisms.

Elemental analysis for C$_{22}$H$_{20}$F$_6$N$_2$O$_4$ Calcd: C 53.88, H 4.11, N 5.71 Found: C 53.69, H 3.99, N 5.74

$^1$H-NMR (CDCl$_3$) δ: 1.26 (3H,d,J=7 Hz), 2.68 (1H,bs), 3.77–3.99 (2H,m), 4.37 (2H,t,J=11.8 Hz), 4.76 (1H,q,J=7

Hz), 4.85 (1H,bs), 6.07 (1H,tt,J=53 Hz,4.6 Hz), 6.46 (1H, d,J=3 Hz), 6.54 (1H,d,J=3 Hz), 6.76–7.00 (2H,m), 6.99 (2H,dt,J=9 Hz, 2.4 Hz), 7.53 (2H,dt,J=9 Hz,2.4 Hz), 7.68–7.84 (1H,m)

Example 30

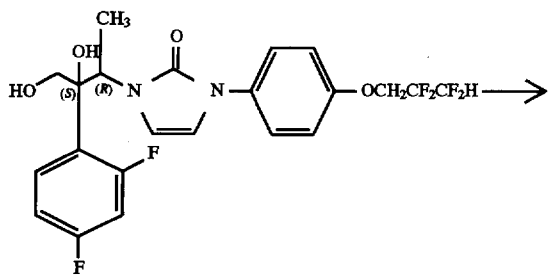

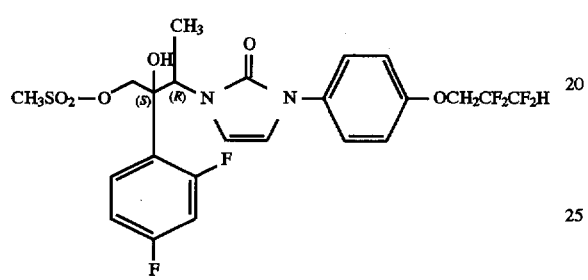

1-[(1R,2S)-2-(2,4-Difluorophenyl)-2,3-dihydroxy-1-methylpropyl]-3-[4-(2,2,3,3-tetrafluoropropoxy)phenyl]-2(1H,3H)-imidazolone (1.2 g) was dissolved in 25 ml of ethyl acetate, to which 0.29 ml of methanesulfonyl chloride and 0.53 ml of triethylamine were added dropwise with ice cooling. After stirring at 0° C. for 30 minutes, the reaction solution was washed with water (15 ml×2) and 15 ml of an aqueous solution of sodium chloride successively. The organic layer was dried over magnesium sulfate. After the solvent was distilled off under reduced pressure, the residue was purified by silica gel chromatography (silica gel: 50 g, eluent; hexane:ethyl acetate=1:1). The desired fraction was concentrated and the residue was recrystallized from a mixture of 5 ml of diisopropyl ether and 10 ml of hexane to give 1.26 g of 1-[(1R,2S)-2-(2,4-difluorophenyl)-2-hydroxy-3-methanesulfonyloxy-1-methylpropyl]-3-[4-(2, 2,3,3-tetrafluoropropoxy)phenyl]-2(1H,3H)-imidazolone as colorless powdery crystals.

Elemental analysis for $C_{23}H_{22}F_6N_2O_6S$ Calcd: C 48.59, H 3.90, N 4.93 Found: C 48.57, H 3.84, N 4.89

$^1$H-NMR (CDCl$_3$) δ: 1.27 (3H,d,J=7 Hz), 2.91 (3H,s), 4.43 (2H,t,J=11.8 Hz), 4.46–4.71 (3H,m), 6.07 (1H,tt,J=53 Hz, 4.8 Hz), 6.44 (1H,d,J=3 Hz), 6.57 (1H,d,J=3 Hz), 6.80–7.05 (2H, m), 7.00 (2H,d,J=9.2 Hz), 7.54 (2H,d,J=9.2 Hz), 7.78–7.92 (1H,m)

Example 31

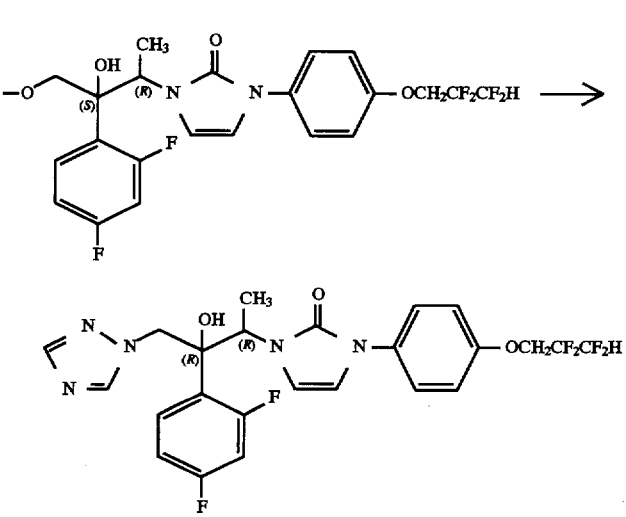

1-[(1R, 2S)-2-(2,4-Difluorophenyl)-2-hydroxy-3-methanesulfonyloxy-1-methylpropyl]-3-[4-(2,2,3,3-tetrafluoropropoxy)phenyl]-2(1H, 3H)-imidazolone(0.55 g) was dissolved in 15 ml of dimethylformamide, to which 0.329 g of 1H-1,2,4-triazole and 1.34 g of potassium carbonate were added. The mixture was heated at 90° C. for 5 hours. After cooling, the reaction solution was diluted with 60 ml of ethyl acetate, and washed with 30 ml of water, 1N-hydrochloric acid (30 ml×2) and 30 ml of an aqueous solution of sodium chloride successively. The organic layer was dried over magnesium sulfate. After the solvent was distilled off under reduced pressure, the residue was purified by silica gel chromatography (silica gel: 50 g, eluent; hexane:ethyl acetate=2:1). The desired fraction was concentrated and the residue was recrystallized from a mixture of 2 ml of ethyl acetate and 10 ml of diisopropyl ether to give 0.25 g of 1-[(1R,2S)-2-(2,4-difluorophenyl)-2-hydroxy-1-methyl-3-(1H-1,2,4-triazol-1-yl)propyl]-3-[4-(2,2,3,3-tetrafluoropropoxy)phenyl]-2(1H,3H)-imidazolone (yield: 47%) as colorless powdery crystals.

The enantiomer excess (ee) of this product was determined to be >99% by HPLC using Chiral Pak AD.

Elemental analysis for $C_{24}H_{21}F_6N_5O_3$ Calcd: C 53.24, H 3.91, N 12.93 Found: C 53.19, H 3.74, N 12.71

$^1$H-NMR (CDCl$_3$) δ: 1.20 (3H,d,J=7 Hz), 4.20 (1H,d, J=14 Hz), 4.38 (2H,t,J=12 Hz), 4.95 (1H,q,J=7 Hz), 5.10 (1H,d, J=14 Hz), 5.51–5.75 (1H,bs), 6.07 (1H,tt,J=53 Hz,5 Hz), 6.60 (1H,d,J=3 Hz), 6.72(1H,d,J=3 Hz), 6.73–6.85 (2H,m), 7.01 (2H, d,J=9 Hz), 7.46–7.57 (1H,m), 7.57 (2H, d,J=9 Hz), 7.74 (1H,s), 7.86 (1H,s)

Example 32

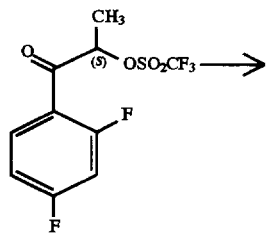

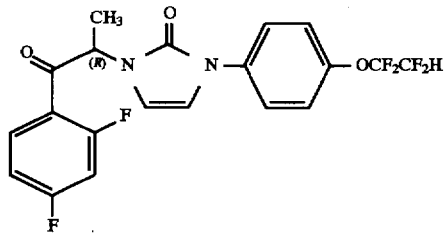

1-[4-(1,1,2,2-Tetrafluoroethoxy)phenyl]-2(1H,3H)-imidazolone (1.42 g) was dissolved in 10 ml of 1-methyl-2-pyrrolidone, to which 60% sodium hydride in oil (0.198 g) was added. The mixture was stirred at room temperature for 30 minutes. The reaction solution was ice-cooled and added dropwise under nitrogen atmosphere over the period of 10 minutes to a solution of 1.8 g of (2S)-2', 4'-difluoro-2-trifluoromethanesulfonyloxypropiophenone in 50 ml of tetrahydrofuran which was cooled to −40° C. Then, the reaction temperature was raised to −20° C. over the period of 20 minutes and the reaction solution was stirred for 10 minutes. The reaction solution was diluted with 3.5 ml of acetic acid and 70 ml of ethyl acetate, washed with water (40 ml×2), 0.5N-hydrochloric acid (40 ml×2) and 40 ml of a saturated aqueous solution of sodium chloride successively, and dried over anhydrous magnesium chloride. After the solvent was distilled off under reduced pressure, the residue was purified by silica gel chromatography (silica gel: 300 g, eluent; hexane:ethyl acetate:acetic acid=2:1:0.08) to give 0.94 g of 1-[(1R)-2-(2,4-difluorophenyl)-2-oxo-1-methylethyl]-3-[4-(1,1,2,2-tetrafluoroethoxy)phenyl]-2(1H,3H)-imidazolone as a pale yellow viscous substance. The product was crystallized from a mixture of diisopropyl ether and hexane to give colorless powdery crystals.

mp 71°–72° C.

[α]$_D^{25}$+6.9° (c=1.0, in methanol)

$^1$H-NMR (CDCl$_3$) δ: 1.63 (3H,d,J=7 Hz), 5.74 (1H,d,J=7 Hz), 5.90 (1H,tt,J=53 Hz,2.8 Hz), 6.58 (1H,d,J=3 Hz), 6.62 (1H,d, J=3 Hz), 6.86–7.05 (2H,m), 7.26 (2H,dt,J=9 Hz,2.4 Hz), 7.53 (2H,dt,J=9 Hz,2.4 Hz), 7.93–8.05 (1H,m)

Example 33

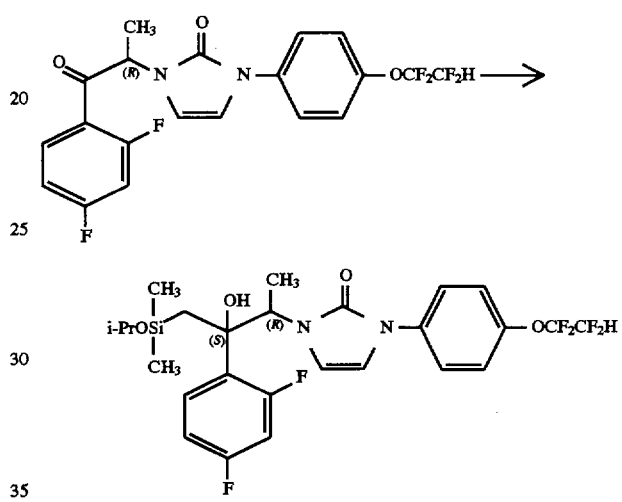

Chloromethylisopropoxydimethyl silane (2.14 g) and 0.313 g of magnesium (for Grignard reaction) were added to 15 ml of tetrahydrofuran and the mixture was heated to 50° C. After adding magnesium tips which were activated with methyl iodide, the mixture was stirred at 50° C. for 3 hours.

The solution containing the Grignard reagent thus obtained was ice-cooled and a solution of 1.2 g of 1-[(1R)-2-(2,4-difluorophenyl)-2-oxo-1-methylethyl]-3-[4-(1,1,2,2-tetrafluoroethoxy)phenyl]-2(1H,3H)-imidazolone in 10 ml of tetrahydrofuran was added thereto dropwise over the period of 5 minutes. The mixture was stirred at room temperature for 15 minutes and then ice-cooled. To the ice cooled mixture was added 10 ml of a cooled saturated aqueous solution of ammonium chloride and 20 ml of cooled water. The mixture was extracted with 80 ml of ethyl acetate. The extract was washed with an aqueous solution of sodium chloride, dried over magnesium sulfate and concentrated under reduced pressure. The residue was purified by silica gel chromatography (silica gel: 100 g, eluent; hexane:ethyl acetate=7:2). The desired fraction was concentrated and the residue was recrystallized from a mixture of 5 ml of diisopropyl ether and 10 ml of hexane to give 0.91 g of 1-[(1R, 2S)-2-(2,4-difluorophenyl)-2-hydroxy-3-(isopropoxydimethylsilyl)-1-methylpropyl]-3-[4-(1,1,2,2-tetrafluoroethoxy)phenyl]-2(1H,3H)-imidazolone (yield: 60%) as colorless needles.

Elemental analysis for $C_{26}H_{30}F_6N_2O_4Si$ Calcd: C 54.16, H 5.24, N 4.86 Found: C 54.06, H 5.29, N 4.90

Example 34

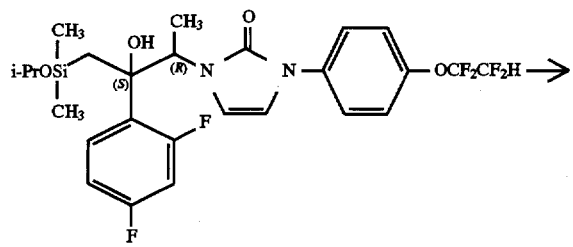

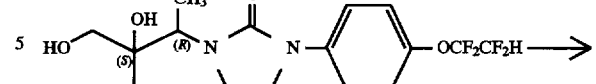

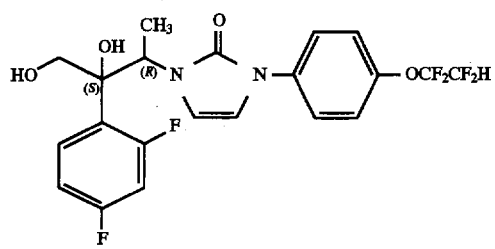

1-[(1R,2S)-2-(2,4-Difluorophenyl)-2-hydroxy-3-(isopropoxydimethylsilyl)-1-methylpropyl]-3-[4-(1,1,2,2-tetrafluoroethoxy)phenyl]-2(1H,3H)-imidazolone (0.88 g) was dissolved in a mixture of methanol and tetrahydrofuran (1:1, 10 ml), to which 1.57 ml of 30% aqueous hydrogen peroxide and 0.128 g of sodium hydrogencarbonate were added. The mixture was heated at 70° to 80° C. for 90 minutes, cooled and extracted with 50 ml of ethyl acetate. The extract was washed with 25 ml of water, an aqueous solution of $Na_2S_2O_3$ (25 ml×2) and 25 ml of an aqueous solution of sodium chloride successively, and dried over magnesium sulfate. After the solvent was distilled off under reduced pressure, the residue was purified by silica gel chromatography (silica gel: 50 g, eluent; hexane:ethyl acetate=2:3) and recrystallized from diisopropyl ether to give 0.5 g of 1-[(1R,2S)-2-(2,4-difluorophenyl)-2,3-dihydroxy-1-methylpropyl]-3-[4-(1,1,2,2-tetrafluoroethoxy)phenyl]-2(1H,3H)-imidazolone (yield: 69%) as colorless powdery crystals.

$^1$H-NMR (CDCl$_3$) δ: 1.26(3 Hz,d,J=7 Hz), 2.57 (1H,bs), 3.76–3.99 (2H,m), 4.79 (1H,q,J=7 Hz), 5.92 (1H,tt,J=53 Hz, 2.8 Hz), 6.50 (1H,d,J=3 Hz), 6.59 (1H,d,J=3 Hz), 6.79–6.97 (2H, m), 7.29 (2H,d,J=9 Hz), 7.69 (2H,d,J=9 Hz), 7.68–7.85 (1H,m)

Example 35

1-[(1R,2S)-2-(2,4-Difluorophenyl)-2,3-dihydroxy-1-methylpropyl]-3-[4-(1,1,2,2-tetrafluoroethoxy)phenyl]-2(1H,3H)-imidazolone (0.5 g) was dissolved in 20 ml of ethyl acetate, to which 0.12 ml of methanesulfonyl chloride and 0.22 ml of triethylamine were added dropwise with ice cooling. After stirring at 0° C. for 30 minutes, the reaction solution was washed with water (10 ml×2) and 10 ml of an aqueous solution of sodium chloride successively. The organic layer was dried over magnesium sulfate. After the solvent was distilled off under reduced pressure, the residue was purified by silica gel chromatography (silica gel: 50 g, eluent; hexane:ethyl acetate=1:1). The desired fraction was concentrated to give 0.58 g of 1-[(1R,2S)-2-(2,4-difluorophenyl)-2-hydroxy-3-methanesulfonyloxy-1-methylpropyl]-3-[4-(1,1,2,2-tetrafluoroethoxy)phenyl]-2(1H,3H)-imidazolone as a colorless oil.

$^1$H-NMR (CDCl$_3$) δ: 1.27 (3 Hz,d,J=7 Hz), 2.90 (3H,s), 4.45–4.72 (3H,m), 5.93 (1H,tt,J=53 Hz,2.8 Hz), 6.49 (1H,d, J=3 Hz), 6.62 (1H,d,J=3 Hz), 6.81–7.00 (2H,m), 7.30 (2H,d, J=9.2 Hz), 7.64 (2H,d,J=9.2 Hz), 7.78–7.92 (1H,m)

Example 36

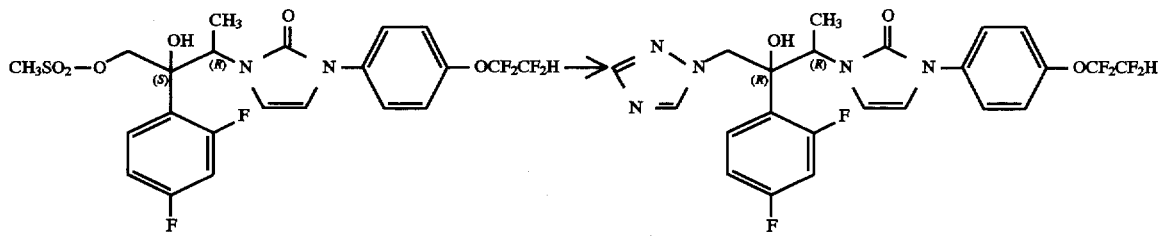

1-[(1R,2S)-2-(2,4-Difluorophenyl)-2-hydroxy-3-methanesufonyloxy-1-methylpropyl]-3-[4-(1,1,2,2-tetrafl##uoroethoxyphenyl]-2(1H,3H)-imidazolone (0.55 g) was dissolved in 15 ml of dimethylformamide, to which 0.336 g of 1H-1,2,4-triazole and 1.37 g of potassium carbonate were added. The mixture was heated at 90° C. for 5 hours. The reaction solution was cooled, diluted with 60 ml of ethyl acetate, and washed with 30 ml of water, 1N-hydrochloric acid (30 ml×2) and 30 ml of an aqueous solution of sodium chloride successively. The organic layer was dried over magnesium sulfate. After the solvent was distilled off under reduced pressure, the residue was purified by silica gel chromatography (silica gel: 50 g, eluent; hexane:ethyl acetate=1:2). The desired fraction was concentrated and the residue was recrystallized from a mixture of 2 ml of ethyl acetate and 10 ml of diisopropyl ether to give 0.24 g of 1-[(1R,2R)-2-(2,4-difluorophenyl)-2-hydroxy-1-methyl-3-(1H-1,2,4-triazole-1-yl)propyl]-3-[4-(1,1,2,2-tetrafluoroethoxy)phenyl]-2(1H,3H)-imidazolone (yield: 46%) as colorless powdery crystals.

The enantiomer excess (ee) of this product was determined to be >99% by HPLC using Chiral Pak AD.

Elemental analysis for $C_{23}H_{19}F_6N_5O_3$ Calcd: C 52.38, H 3.63, N 13.28 Found: C 52.12, H 3.65, N 13.19

$^1$H-NMR (CDCl$_3$) δ: 1.20 (3H,d,J=7 Hz), 4.19 (1H,d, J=14 Hz), 4.97 (1H,q,J=7 Hz), 5.10 (1H,d,J=14 Hz), 5.40–5.62 (1H,bs), 5.93 (1H,tt,J=2,8 Hz), 6.64 (1H,d,J=3 Hz), 6.77 (1H, d,J=3 Hz), 6.75–6.85 (2H,m), 7.30 (2H,d,J=9 Hz), 7.41–7.55 (1H,m), 7.68 (2H,d,J=9 Hz), 7.74 (1H,s), 7.85 (1H,s)

Example 37

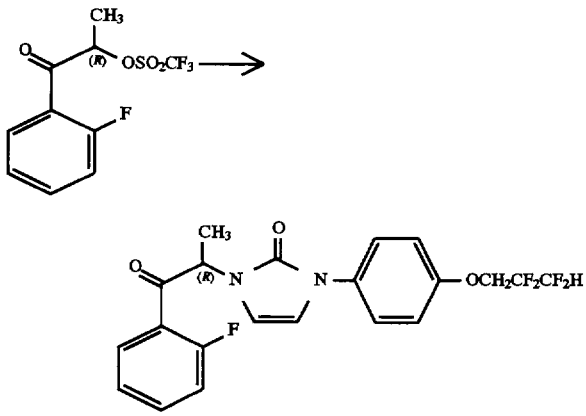

1-[4-(2,2,3,3-Tetrafluoropropoxy)phenyl]-2(1H,3H)-imidazolone (4.6 g) was dissolved in 30 ml of 1-methyl-2-pyrrolidone, to which 0.6 g of 60% sodium hydride in oil was added. The mixture was stirred at room temperature for 0.5 hours. The reaction solution was ice-cooled and added dropwise under nitrogen atmosphere over the period of 5 minutes to a solution of 5.3 g of (2S)-2'-fluoro-2-trifluoromethanesulfonyloxypropiophenone in 50 ml of tetrahydrofuran which was cooled to –40° C. Then, the reaction solution was stirred at –40° to –35° C. for 20 minutes. To the reaction solution was added 2 ml of acetic acid. The mixture was diluted with a mixture of 300 ml of ethyl acetate and 150 ml of diisopropyl ether, washed with 80 ml of water, 0.5N-hydrochloric acid (80 ml×2) and 40 ml of an aqueous solution of sodium chloride successively, and dried over anhydrous magnesium sulfate. The solvent was distilled off under reduced pressure. The residue was purified by silica gel chromatography (silica gel: 200 g, eluent; hexane:ethyl acetate:acetic acid=2:1:0.03) and crystallized from diisopropyl ether to give 2.6 g of 1-[(1R)-2-(2-fluorophenyl)-2-oxo-1-methylethyl]-3-[4-(2,2,3,3-tetrafluoropropoxy)phenyl]-2(1H,3H)-imidazolone as colorless powdery crystals.

The enantiomer excess (ee) of this product was determined to be 98.8% by HPLC using Chiral Pak AD.

mp 71°–73° C.

$^1$H-NMR (CDCl$_3$) δ: 1.63 (3H,d,J=7.2 Hz), 4.35 (2H,tt, J=11.8 Hz,J=1.4 Hz), 5.80 (1H,q,J=7.2 Hz), 6.07 (1H,tt,J=53 Hz, J=4.6 Hz), 6.57 (2H,s), 6.97 (2H,d,J=9 Hz), 7.13–7.30 (2H,m), 7.48–7.64 (1H,m), 7.53 (2H,d,J=9 Hz), 7.93 (1H, dt,J=1,8 Hz, J=7.6 Hz)

$[\alpha]_D^{23}$+8.5° (c=1.02, in methanol)

Elemental analysis for $C_{21}F_{17}F_5N_2O_3$ Calcd: C 57.28, H 3.89, N 6.36 Found: C 57.34, H 3.78, N 6.12

Example 38

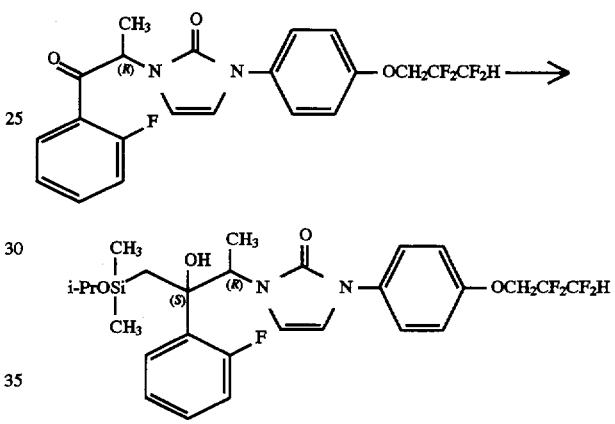

Chloromethylisopropoxydimethyl silane (8.5 g) and 1.24 g of magnesium (for Grignard reaction) were added to 50 ml of tetrahydrofuran and the mixture was heated to 50° C. After adding magnesium tips which were activated with methyl iodide, the mixture was stirred at 50° C. for 5 hours. The solution containing the Grignard reagent thus obtained was ice-cooled and a solution of 1-[(1R)-2-(2-fluorophenyl)-2-oxo-1-methylethyl]-3-[4-(2,2,3,3-tetrafluoropropoxy)phenyl]-2(1H,3H)-imidazolone (4.5 g, 98.8% ee) in 25 ml of tetrahydrofuran was added thereto dropwise over the period of 20 minutes. The mixture was stirred at room temperature for 30 minutes and ice-cooled. To the ice cooled mixture was added 25 ml of a cooled saturated aqueous solution of ammonium chloride and 25 ml of cooled water. The mixture was extracted with a mixture of 100 ml of ethyl acetate and 50 ml of diisopropyl ether. The extract was washed with an aqueous solution of sodium chloride, dried over magnesium sulfate and concentrated under reduced pressure. The residue was recrystallized from a mixture of diisopropyl ether and ethyl acetate to give 2.67 g of 1-[(1R,2S)-2-(2-fluorophenyl)-2-hydroxy-3-(isopropoxydimethylsilyl)- 1-methylpropyl]-3-[4-(2,2,3,3-tetrafluoropropoxy)phenyl]-2(1H,3H)-imidazolone as colorless powdery crystals.

The mother liquor of recrystallization was concentrated. The residue was purified by silica gel chromatography (silica gel: 150 g, eluent; hexane:ethyl acetate=2:1) and recrystallized from a mixture of diisopropyl ether and hexane to give 0.78 g of the above compound (total yield: 59%).

mp 151°–152° C.

[α]$_D^{22}$=+13.1° (c=1.0, in methanol)

Elemental analysis for $C_{27}H_{33}F_5N_2O_4Si$ Calcd: C 56.63, H 5.81, N 4.89 Found: C 56.51, H 5.91, N 5.02

Example 39

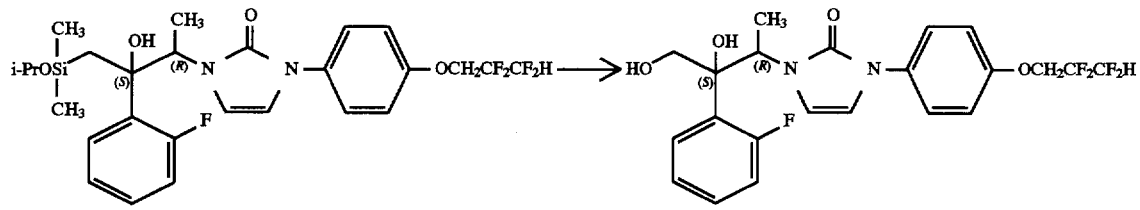

1-[(1R,2S)-2-(2-(Fluorophenyl)-2-hydroxy-3-(isopropoxydimethylsilyl)-1-methylpropyl]-3-[4-(2,2,3,3-tetrafluoropropoxy)phenyl]-2(1H,3H)-imidazolone (3.37 g) was dissolved in a mixture of methanol and tetrahydrofuran (1:1, 30 ml), to which 6.1 ml of 30% aqueous hydrogen peroxide and 0.50 g of sodium hydrogencarbonate were added, and the mixture was heated at 80° C. for 110 minutes. The reaction solution was cooled and extracted with 120 ml of ethyl acetate. The extract was washed with water (20 ml×2), an aqueous solution of $Na_2S_2O_3$ (20 ml×2) and 10 ml of an aqueous solution of sodium chloride successively, and dried over magnesium sulfate. The solvent was distilled off under reduced pressure. The residue was purified by silica gel chromatography (silica gel: 50 g, eluent; hexane:ethyl acetate=1:1) and recrystallized from a mixture of methanol and diisopropyl ether to give 1.99 g of 1-[(1R,2S)-2-(2-fluorophenyl)-2,3-dihydroxy-1-methylpropyl]-3-[4-(2,2,3,3-tetrafluoropropoxy)phenyl]-2(1H,3H)-imidazolone (yield: 72%) as colorless prisms.

mp 166°–167° C.

[α]$_D^{22}$+2.0° (c=1.01, in methanol)

Elemental analysis for $C_{22}H_{21}F_5N_2O_4$ Calcd: C 55.93, H 4.48, N 5.93 Found: C 55.77, H 4.41, N 6.16

$^1$H-NMR (CDCl$_3$) δ: 1.28 (3H,d,J=7.2 Hz), 2.61 (1H,br), 3.78–4.00 (2H,m), 4.38 (2H,tt,J=11.8 Hz,J=1.4 Hz), 4.80 (1H, br), 4.85 (1H,q,J=7.2 Hz), 6.08 (1H,tt,J=53 Hz,J=4,8 Hz), 6.49 (1H,d,J=3 Hz), 6.55 (1H,d,J=3 Hz), 7.01 (2H,dt, J=9 Hz,J=1.8 Hz), 7.02–7.40 (3H,m), 7.55 (2H,dt,J=9 Hz,J= 1.8 Hz), 7.76 (1H,dt, J=1.8 Hz,8 Hz)

Example 40

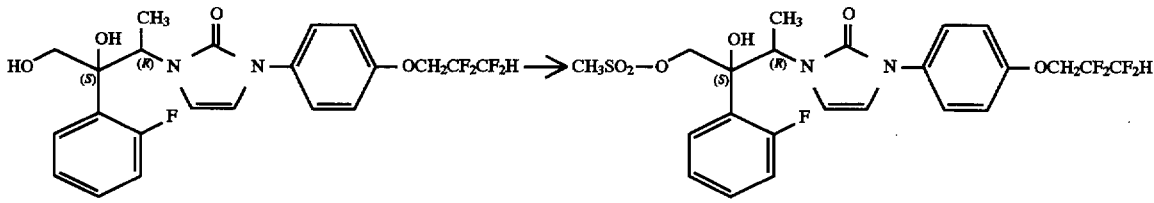

1-[(1R,2S)-2-(2-Fluorophenyl)-2,3-dihydroxy-1-methylpropyl]-3-[4-(2,2,3,3-tetrafluoropropoxy)phenyl]-2 (1H,3H)-imidazolone (1.90 g) was dissolved in 30 ml of ethyl acetate, to which 0.69 g of methanesulfonyl chloride and 0.61 g of triethylamine were added dropwise with ice cooling. After stirring at 0° C. for 30 minutes, the reaction solution was washed with water (20 ml×2) and 10 ml of an aqueous solution of sodium chloride successively. The organic layer was dried over magnesium sulfate. The solvent was distilled off under reduced pressure to give 2.2 g of 1-[(1R,2S)-2-(2-fluorophenyl)-2-hydroxy-3-methanesulfonyloxy-1-methylpropyl]-3-[4-(2,2,3,3-tetrafluoropropoxy)phenyl]-2(1H,3H)-imidazolone as a colorless oil.

$^1$H-NMR (CDCl$_3$) δ: 1.28 (3H,d,J=7 Hz), 2.89 (3H,s), 4.38 (2H,tt,J=11.8 Hz,J=1.6 Hz), 4.53 (1H,dd,J=11 Hz,J=1.8 Hz), 4.68 (1H,q,J=7 Hz), 4.73 (1H,d,J=11.8 Hz), 6.08 (1H, tt,J=53 Hz, J=5 Hz), 6.47 (1H,d,J=3 Hz), 6.58 (1H,d,3 Hz), 7.02 (2H,d, J=9 Hz), 7.05–7.43 (3H,m), 7.55 (2H,d,J=9 Hz), 7.81 (1H,dt, J=1.8 Hz,J=8 Hz)

Example 41

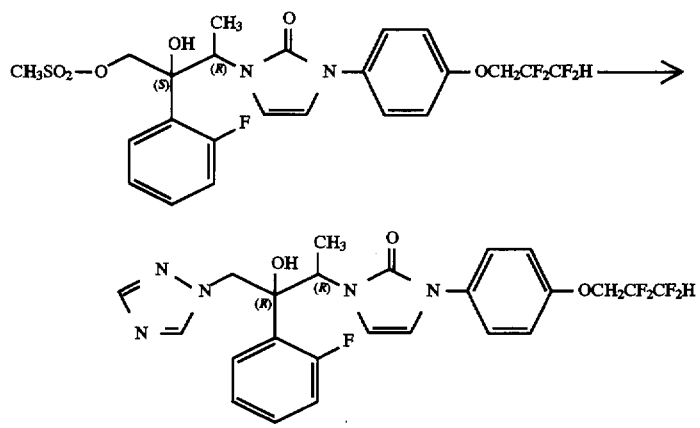

1-[(1R,2S)-2-(2-Fluorophenyl)-2-hydroxy-3-methanesulfonyloxy-1-methylpropyl]-3-[4-(2,2,3,3-tetrafluoropropoxy)phenyl]-2(1H,3H)-imidazolone (2.2 g) was dissolved in 40 ml of dimethylformamide, to which 1.39 g of 1H-1,2,4-triazole and 5.55 g of potassium carbonate were added. The mixture was heated at 80° C. for 4 hours. The reaction solution was diluted with a mixture of 150 ml of ethyl acetate and 50 ml of diisopropyl ether, and washed with water (40 ml×2), 1N-hydrochloric acid (40 ml×2) and 20 ml of aqueous solution of sodium chloride successively. The organic layer was dried over magnesium sulfate. After the solvent was distilled off under reduced pressure, the residue was purified by silica gel chromatography (silica gel: 50 g, eluent; hexane:ethyl acetate=1:1 to 1:2). The desired fraction was concentrated and the residue was recrystallized from a mixture of ethyl acetate and diisopropyl ether to give 1.59 g of 1-[(1R,2S)-2-(2-fluorophenyl)-2-hydroxy-1-methyl-3-(1H-1,2,4-triazol-1-yl)propyl]-3-[4-(2,2,3,3-tetrafluoropropoxy)phenyl]-2(1H,3H)-imidazolone (yield: 75%) as colorless powdery crystals.

Elemental analysis for $C_{24}H_{22}F_5N_5O_3$ Calcd: C 55.07, H 4.24, N 13.38 Found: C 54.85, H 4.11, N 13.31

$^1$H-NMR (CDCl$_3$) δ: 1.20 (3H,d,J=7 Hz), 4.21 (1H,d, J=14 Hz), 4.38 (2H,tt,J=11.8 Hz,J=1.4 Hz), 5.03 (1H,q=7 Hz), 5.16 (1H,d,J=14 Hz), 5.42 (1H,br), 6.08 (1H,tt,J=53 Hz,J=5 Hz), 6.60 (1H,d,J=3.2 Hz), 6.77 (1H,d,J=3.2 Hz), 6.97–7.10 (2H,m), 7.01 (2H,dt,J=9 Hz,J=2.2 Hz), 7.18–7.30 (1H,m), 7.44–7.54 (1H, m), 7.59 (2H,dt,J=9 Hz,J=2.2 Hz), 7.73 (1H,s), 7.82 (1H,s)

$[α]_D^{22}$ −21.7° (c=1.0, in methanol)

Example 42

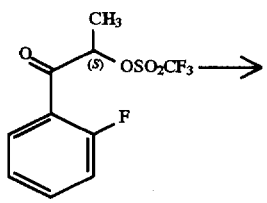

1-[4-(1,1,2,2-Tetrafluoroethoxy)phenyl]-2(1H,3H)-imidazolone (9.7 g) was dissolved in 60 ml of 1-methyl-2-pyrrolidone, to which 1.08 g of 72% sodium hydride in oil was added. The mixture was stirred at room temperature for an hour. The reaction solution was ice-cooled and added dropwise under nitrogen atmosphere over the period of 25 minutes to a solution of 11.6 g of (2S)-2'-fluoro-2-trifluoromethanesulfonyloxypropiophenone in 100 ml of tetrahydrofuran which was cooled to −40° C. After the reaction temperature was raised to −35° C. over the period of 10 minutes, the reaction solution was stirred for 20 minutes. The reaction solution was diluted with 3 ml of acetic acid, 450 ml of ethyl acetate and 200 ml of diisopropyl ether, washed with water (250 ml×2), 0.5N-hydrochloric acid (150 ml×2) and 300 ml of a saturated aqueous solution of sodium chloride successively, and dried over anhydrous magnesium sulfate. After the solvent was distilled off under reduced pressure, the residue was purified by silica gel chromatography (eluent; hexane:ethyl acetate:acetic acid= 2:1:0.04) and crystallized from diisopropyl ether to give 5.1 g of 1-[(1R)-2-(2-fluorophenyl)-2-oxo-1-methylethyl]-3-[4-(1,1,2,2-tetrafluoroethoxy)phenyl]-2(1H,3H)-imidazolone (yield: 34%) as colorless prisms.

The enantiomer excess (ee) of this product was determined to be 99.9% by HPLC using Chiral Pak AD.

$^1$H-NMR (CDCl$_3$) δ: 1.63 (3H,d,J=7 Hz), 5.79 (1H,q,J=7 Hz), 5.92 (1H,tt,J=53 Hz,3 Hz), 6.60 (1H,d,J=3 Hz), 6.63 (1H,d, J=3 Hz), 7.13–7.30 (2H,m), 7.26 (2H,d,J=9 Hz), 7.51–7.64 (1H, m), 7.63 (2H,d,J=9 Hz), 7.93 (1H,dt,J=8 Hz,2 Hz)

mp 78°–79° C.

$[α]_D^{23}$ +4.6° (c=1.0, in methanol)

Elemental analysis for $C_{20}H_{15}F_5N_2O_3$ Calcd: C 56.34, H 3.55, N 6.57 Found: C 56.20, H 3.61, N 6.41

Example 43

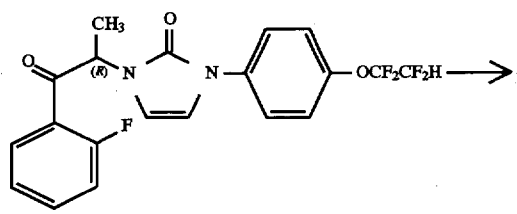

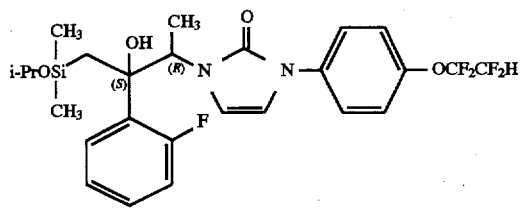

Chloromethylisopropoxydimethyl silane (8.5 g) and 1.24 g of magnesium (for Grignard reaction) were added to 50 ml of tetrahydrofuran and the mixture was heated to 60° C. After adding magnesium tips which were activated with methyl iodide, the mixture was stirred at 80° C. for 3 hours.

The solution containing the Grignard reagent thus obtained was ice-cooled and a solution of 1-[(1R)-2-(2-fluorophenyl)-2-oxo-1-methylethyl]-3-[4-(1,1,2,2-tetrafluoroethoxy)phenyl]-2(1H,3H)-imidazolone (5.1 g, 99.9 ee) in 30 ml of tetrahydrofuran was added thereto dropwise over the period of 40 minutes. The mixture was stirred at room temperature for 45 minutes. The reaction solution was ice-cooled, and 40 ml of a cooled saturated aqueous solution of ammonium chloride and 60 ml of cooled water were added thereto. The mixture was extracted with a mixture of 150 ml of ethyl acetate and 50 ml of diisopropyl ether. The extract was washed with an aqueous solution of sodium chloride, dried over magnesium sulfate and concentrated under reduced pressure. The residue was purified by silica gel chromatography (eluent; hexane:ethyl acetate=3:1) to give 5.7 g of 1-[(1R,2S)-2-(2-fluorophenyl)-2-hydroxy-3-(isopropoxydimethylsilyl)-1-methylpropyl]-3-[4-(1,1,2,2-tetrafluoroethoxy)phenyl]-2(1H,3H)-imidazolone (yield: 86%) as a colorless oil.

$^1$H-NMR (d$_6$-DMSO) δ: −0.35 (3H,s), −0.30 (3H,s), 0.94–1.09 (4H,m), 0.98 (6H,d,J=6 Hz), 1.56 (1H,dd,J=15 Hz,2 Hz), 3.79 (1H,septet,J=6 Hz), 4.73 (1H,q,J=7 Hz), 5.16 (1H,br), 6.82 (1H,tt,J=52 Hz,3 Hz), 6.85 (1H,d,J=3 Hz), 7.14 (1H,d, J=3 Hz), 7.17–7.56 (3H,m), 7.38 (2H,d,J=9 Hz), 7.69 (1H,t, J=8 Hz), 7.89 (2H,d,J=9 Hz)

IR (neat): 3420, 2960, 2890, 1680, 1610, 1510 cm$^{-1}$

Example 44

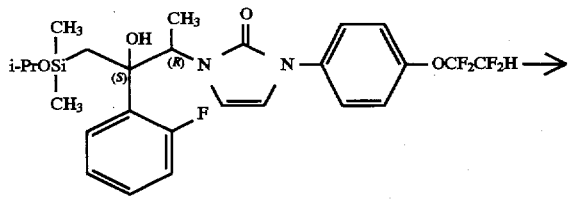

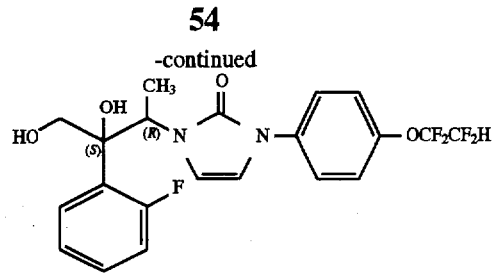

1-[(1R,2S)-2-(2-Fluorophenyl)-2-hydroxy-3-(isopropoxydimethylsilyl)-1-methylpropyl]-3-[4-(1,1,2,2-tetrafluoroethoxy)phenyl]-2(1H,3H)-imidazolone (5.5 g) was dissolved in a mixture of methanol and tetrahydrofuran (1:1, 50 ml), to which 10 ml of 30% aqueous hydrogen peroxide and 0.82 g of sodium hydrogencarbonate were added. The mixture was heated at 80° to 85° C. for 2 hours. The reaction solution was cooled and extracted with 200 ml of ethyl acetate. The extract was washed with 100 ml of water, an aqueous solution of Na$_2$S$_2$O$_3$ (100 ml×2) and 100 ml of an aqueous solution of sodium chloride successively, and dried over magnesium sulfate. The solvent was distilled off under reduced pressure. The residue was purified by silica gel chromatography (eluent; hexane:ethyl acetate=1:1) and recrystallized from a mixture of methanol and diisopropyl ether to give 2.7 g of 1-[(1R,2S)-2-(2-fluorophenyl)-2,3-dihydroxy-1-methylpropyl]-3-[4-(1,1,2,2-tetrafluoroethoxy)phenyl]-2(1H,3H)-imidazolone (yield: 60%) as colorless powdery crystals.

mp 175°–176° C.

Elemental analysis for C$_{21}$H$_{19}$F$_5$N$_2$O$_4$ Calcd: C 55.03, H 4.18, N 6.11 Found: C 54.84, H 4.12, N 6.24

$^1$H-NMR (CDCl$_3$) δ: 1.26 (3H,d,J=7 Hz), 2.60 (1H,br), 3.75–3.88 (1H,m), 3.88–4.02 (1H,m), 4.68 (1H,br), 4.88 (1H, q,J=7 Hz), 5.94 (1H,tt,J=53 Hz,3 Hz), 6.55 (1H,d,J=3 Hz), 6.60 (1H,d,J=3 Hz), 7.01–7.40 (3H,m), 7.29 (2H,d,J=9 Hz), 7.65 (2H, d,J=9 Hz), 7.75 (1H,t,J=8 Hz)

Example 45

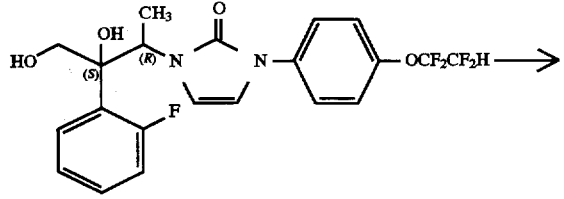

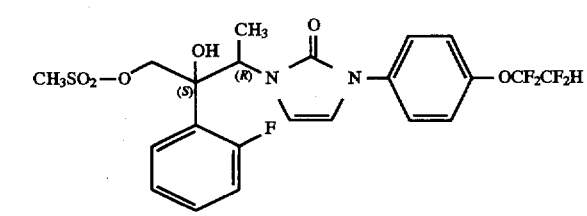

1-[(1R,2S)-2-(2-Fluorophenyl)-2,3-dihydroxy-1-methylpropyl]-3-[4-1,1,2,2-tetrafluoroethoxy)phenyl]-2(1H,3H)-imidazolone (2.6 g) was dissolved in 50 ml of ethyl acetate, to which 1.6 g of methanesulfonyl chloride and 1.4 g of triethylamine were added dropwise with ice cooling. After stirring at 0° C. for 3 hours, the reaction solution was washed with water (80 ml×2) and 800 ml of an aqueous solution of sodium chloride successively. The organic layer was dried over magnesium sulfate. The solvent was distilled off under reduced pressure to give 3.6 g of 1-[(1R,2S)-2-(2-fluorophenyl)-2-hydroxy-3-methanesulfonyloxy-1-methylpropyl]-3-[4-(1,1,2,2-tetrafluoroethoxy)phenyl]-2(1H,3H)-imidazolone as a colorless oil.

Example 46

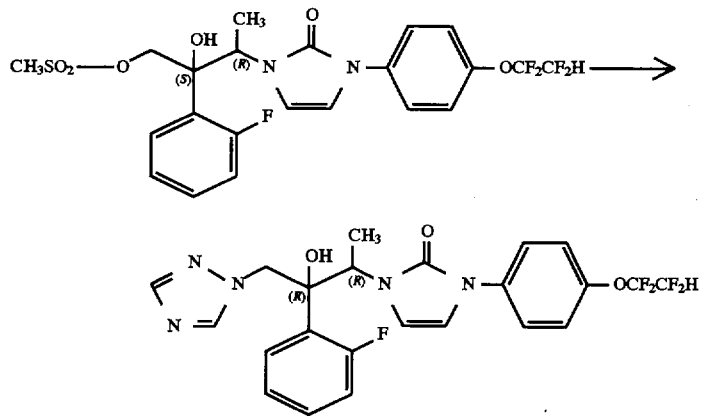

1-[(1R,2S)-2-(2-Fluorophenyl)-2-hydroxy-3-methanesulfonyloxy-1-methylpropyl]-3-[4-(1,1,2,2-tetrafluoroethoxy)phenyl]-2(1H,3H)-imidazolone (3.6 g) was dissolved in 70 ml of dimethylformamide, to which 2.0 g of 1H-1,2,4-triazole and 7.8 g of potassium carbonate were added. The mixture was heated at 80° C. for 4 hours. The reaction solution was diluted with a mixture of 150 ml of ethyl acetate and 50 ml of diisopropyl ether, and washed with 150 ml of water, 1N-hydrochloric acid (100 ml×2) and 100 ml of an aqueous solution of sodium chloride successively. The organic layer was dried over magnesium sulfate. After the solvent was distilled off under reduced pressure, the residue was purified by silica gel chromatography (eluent; hexane:ethyl acetate=1:2 to ethyl acetate). The desired fraction was concentrated and the residue was recrystallized from diisopropyl ether to give 2.0 g of 1-[(1R,2S)-2-(2 -fluorophenyl)-2-hydroxy-1-methyl-3-(1H-1,2,4-triazol-1-yl)propyl]-3-[4-(1,1,2,2-tetrafluoroethoxy)phenyl]-2(1H,3H)-imidazolone (yield: 69%) as a colorless powder.

The enantiomer excess (ee) of this product was determined to be >99% by HPLC using Chiral Pak AD.

Elemental analysis for $C_{23}H_{20}F_5N_5O_3$ Calcd: C 54.23, H 3.96, N 13.75 Found: C 54.30, H 3.90, N 13.51

$^1$H-NMR (CDCl$_3$) δ: 1.20 (3H,d,J=7 Hz), 4.19 (1H,d,J=14 Hz), 5.05 (1H,q,J=7 Hz), 5.16 (1H,d,J=14 Hz), 5.26–5.50 (1H,br), 5.93 (1H,tt,J=53 Hz,3 Hz), 6.65 (1H,d,J=3 Hz), 6.81 (1H,d,J=3 Hz), 6.97–7.06 (2H,m), 7.19–7.31 (2H,m), 7.47 (1H, dt,J=8 Hz,2 Hz), 7.69 (2H,d,J=9 Hz), 7.73 (1H,s), 7.81 (1H,s)

$[\alpha]_D^{21}$ –22.0° (c=1.0, in methanol)

Example 47

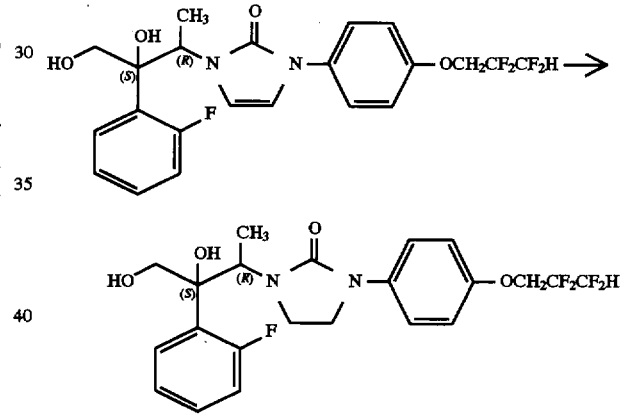

A solution of 1-[(1R,2S)-2-(2-fluorophenyl)-2,3-dihydroxy-1-methylpropyl]-3-[4-(2,2,3,3-tetrafluoropropoxy)phenyl]-2(1H,3H)-imidazolone (1.0 g) in acetic acid (15 ml) was hydrogenated over 10% palladium carbon (50% wet, 0.25 g) under ordinary pressure for 5 hours at room temperature and then 3 hours at 50° C. After cooling, the catalyst was filtered off and the filtrate was evaporated in vacuo. The residue was recrystallized from diisopropyl ether to give 1-[(1R,2S)-2-(2-fluorophenyl)-2,3-dihydroxy-1-methylpropyl]-3-[4-(2,2,3,3-tetrafluoropropoxy)phenyl]-2-imidazolidinone (0.69 g) as a colorless crystalline powder. The mother liquor was concentrated in vacuo and the residue was purified by chromatography on silica gel (eluent; hexane-ethyl acetate, 2:1) followed by crystallization from a mixture of diisopropyl ether and hexane to give the additional product (0.20 g).

mp 139°–140° C. (diisopropyl ether)

$^1$H-NMR (CDCl$_3$) δ: 1.13 (3H,d,J=7.4 Hz), 2.20 (1H,br), 3.56–4.45 (7H,m), 4.33 (2H,t,J=11.9 Hz), 4.98 (1H,br), 6.07 (1H,tt,J=53.2 Hz,J=4.8 Hz), 6.93 (2H,d,J=8,8 Hz), 6.95–7.40 (3H,m), 7.47 (2H,d,J=8.8 Hz), 7.74 (1H,dt,J=1.8 Hz,J=8.2 Hz)

Example 48

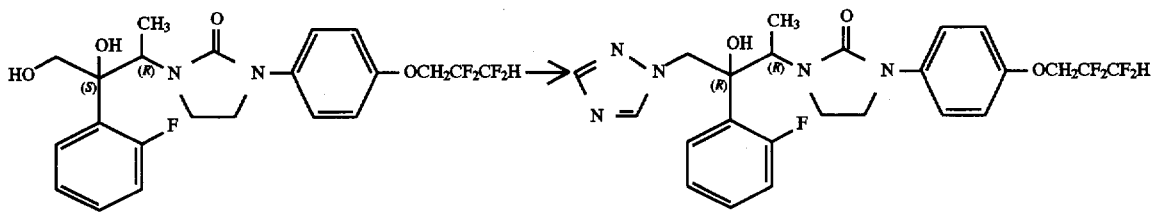

Metanesulfonyl chloride (2.12 g) and triethylamine (1.87 g) were added dropwise to an ice-cooled solution of 1-[(1R,2S)-2-(2-fluorophenyl)-2,3-dihydroxy-1-methylpropyl]-3-[4-(2,2,3,3-tetrafluoropropoxy)phenyl]-2-imidazolidinone (5.85 g) in ethyl acetate (60 ml). The resulting mixture was stirred for 20 minutes at 0° C. and then washed with water (20 ml×2) and an aqueous sodium chloride solution (20 ml) successively. The organic layer was dried over magnesium sulfate and evaporated in vacuo to give 1-[(1R,2S)-2-(2-fluorophenyl)-2-hydroxy-3-methanesulfonyloxy-1-methylpropyl]-3-[4-(2,2,3,3-tetrafluoropropoxy)phenyl]-2-imidazolidinone (6.8 g) as a colorless oil. This compound (6.8 g) was dissolved in N,N-dimethylformamide (130 ml). 1H-1,2,4-Triazole (4.24 g) and potassium carbonate (16.9 g) were added to the solution. The resulting mixture was heated at 80° C. for 5 hours, and then concentrated in vacuo. The residue was diluted with ethyl acetate (200 ml) and the mixture was washed with water (40 ml×2), 1N-hydrochloric acid (40 ml×2) and an aqueous sodium chloride solution successively. The organic layer was dried over magnesium sulfate and evaporated in vacuo. The residue was purified by chromatography on silica gel (100 g; eluent, hexane-ethyl acetate, 2:1 to 1:2) followed by recrystallization from a mixture of ethyl acetate and diisopropyl ether to give 1-[(1R,2R)-2-(2-fluorophenyl)-2-hydroxy-1-methyl-3-(1H-1,2,4-triazol-1-yl)propyl]-3-[4-(2,2,3,3-tetrafluoropropoxy)phenyl]-2-imidazolidinone (4.4 g, 68%) as colorless prisms.

$^1$H-NMR (CDCl$_3$) δ: 1.06 (3H,d,J=7 Hz), 3.62–4.08 (4H,m), 4.34 (2H,tt,J=11.8 Hz,J=1,6 Hz), 4.53 (1H,d,J=14,2 Hz), 4.60–4,80 (1H,m), 5.14 (1H,.d.J=14.2 Hz), 5.31 (1H,br), 6.07 (1H,tt,H=53 Hz.J=5 Hz), 6.94 (2H,d,J=9.2 Hz), 6.90–7.10 (2H,m), 7.15–7.28 (1H,m), 7.36–7.50 (1H,m), 7.52 (2H,d,J=9,2 Hz), 7.74 (1H,S), 7.84 (1H,S)

The present invention provides a method of preparing the optically active triazole compounds of the formulae (I) and (I'), which are useful as a therapeutic agent for fungal infections, in a highly stereoselective and economic manner.

Further, the present invention provides optically active intermediates for the production of the same.

What we claimed is:

1. A compound of the formula (V):

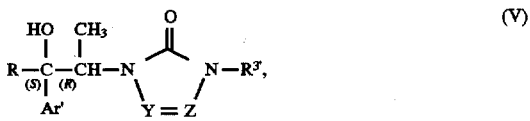

(V)

wherein Ar' is a halogenated phenyl group, R is a hydrocarbon residue having at the α-carbon, a functional group selected from the group consisting of a silyl group, a double bond, and an optionally activated hydroxyl group, R$^{3'}$ is an optionally substituted aliphatic or aromatic hydrocarbon residue or an optionally substituted aromatic heterocyclic group, Y and Z are, the same or different, a nitrogen atom or a methine group optionally substituted with a lower alkyl group, and (R) and (S) represent configurations.

2. The compound according to claim 1, in which the functional group in R of the formula (V) is a silyl group.

3. The compound according to claim 1, in which the functional group in R of the formula (V) is a double bond.

4. The compound according to claim 1, in which the functional group in R of the formula (V) is an optionally activated hydroxyl group.

5. The compound according to claim 1, in which R of the formula (V) is a methylene group having a functional group selected from the group consisting of a silyl group and an optionally activated hydroxyl group.

6. The compound according to claim 1, in which R of the formula (V) is a methine group having a double bond.

7. The compound according to claim 1, in which R of the formula (V) is a group represented by the formula:

$$R'''-\underset{\underset{R''}{|}}{\overset{\overset{R'}{|}}{Si}}-CH_2-,$$

wherein R', R'' and R''' are, the same or different, a lower alkyl group or a lower alkoxy group.

8. The compound according to claim 1, in which R of the formula (V) is H$_2$C=CH—.

9. The compound according to claim 1, in which R of the formula (V) is HO—CH$_2$—.

10. The compound according to claim 1, in which R of the formula (V) is a group represented by R$^5$SO$_3$—CH$_2$— wherein R$^5$ is a lower alkyl group or an optionally substituted phenyl group.

11. The compound according to claim 1, in which Ar' of the formula (V) is a phenyl group substituted with one or two fluorine atoms.

12. The compound according to claim 1, in which Ar' of the formula (V) is 2,4-difluorophenyl or 2-fluorophenyl.

13. The compound according to claim 1, in which R$^{3'}$ of the formula (V) is a phenyl group substituted with a halogeno-alkoxy group.

14. The compound according to claim 1, in which R$^{3'}$ of the formula (V) is 4-(2,2,3,3-tetrafluoropropoxy)phenyl or 4-(1,1,2,2-tetrafluoroethoxy)phenyl.

15. The compound according to claim 1, in which Y and Z of the formula (V) are, the same or different, a nitrogen atom or a methine group.

16. A method of preparing the compound of the formula (V) of claim 1:
which comprises reacting a compound of the formula (II):

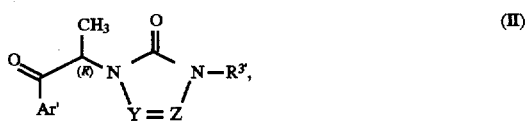

(II)

wherein the symbols have the same meanings as defined above, with a Grignard reagent of the formula (XXXI):

R—MgX    (XXXI), wherein X is a halogen atom and R has the same meaning as defined above.

17. The method according to claim 16, in which the Grignard reagent is a compound of the formula (XI):

$$R'''-\underset{\underset{R''}{|}}{\overset{\overset{R'}{|}}{Si}}-CH_2MgX^2-, \quad (XI)$$

wherein R', R" and R'" are, the same or different, a lower alkyl group or a lower alkoxy group and $X^2$ is a halogen atom.

18. The method according to claim 17, in which R' and R" of the formula (XI) are methyl groups and R'" of the formula (XI) is $(CH_3)_2CHO—$.

19. The method according to claim 16, in which the Grignard reagent is a compound of the formula (XII):

$$H_2C=CH—MgX^3 \quad (XII),$$

wherein $X^3$ is a halogen atom.

20. The method according to claim 17, in which the compound of the formula (V) is oxidized to give a compound of the formula (V'):

$$HO-CH_2-\underset{\underset{Ar'}{|}}{\overset{\overset{HO\ CH_3}{|\ \ \ |}}{C}}-\underset{(R)}{CH}-N\diagdown\diagup N-R^{3'}, \quad (V')$$
$$\qquad\qquad (S)|\ (R)\qquad Y=Z$$

wherein Ar' is a halogenated phenyl group, $R^{3'}$ is an optionally substituted aliphatic or aromatic hydrocarbon residue or an optionally substituted aromatic heterocyclic group, Y and Z are, the same or different, a nitrogen atom or a methine group optionally substituted with a lower alkyl group, and (R) and (S) represent configurations, and then the obtained compound of the formula (V'), after activating a hydroxyl group upon necessity, is reacted with 1H-1,2,4-triazole or a salt thereof to give a compound of the formula (I):

(I)

wherein the symbols have the same meanings as defined above, or a salt thereof.

21. The method according to claim 20, in which the compound of the formula (V) is oxidized using an aqueous solution of hydrogen peroxide as an oxidizing agent.

22. The method according to claim 20, in which the compound of the formula (V) is oxidized in the presence of a base.

23. The method according to claim 20, in which the hydroxyl group is activated using, as an activating agent, a compound of the formula (XIII):

$$R^5SO_2X^4 \quad (XIII),$$

wherein $R^5$ is a lower alkyl group or an optionally substituted phenyl group, and $X^4$ is a halogen atom or a group represented by $R^5SO_3—$ wherein $R^5$ has the same meaning as defined above.

24. A compound of the formula (Va'):

(Va')

wherein Ar' is a halogenated phenyl group, R is a hydrocarbon residue having at the α-carbon, a functional group selected from the group consisting of a silyl group, a double bond, and an optionally activated hydroxyl group, $R^{3'}$ is an optionally substituted aliphatic or aromatic hydrocarbon residue or an optionally substituted aromatic heterocyclic group, and (R) and (S) represent configurations.

25. The compound according to claim 24, in which R of the formula (Va') is $HO—CH_2—$.

26. The compound according to claim 24, in which R of the formula (Va') is a group represented by $R^5SO_3—CH_2—$ wherein $R^5$ is a lower alkyl group or an optionally substituted phenyl group.

27. The compound according to claim 24, in which Ar' of the formula (Va') is a phenyl group substituted with one or two fluorine atoms.

28. The compound according to claim 24, in which Ar' of the formula (Va') is 2,4-difluorophenyl or 2-fluorophenyl.

29. The compound according to claim 24, in which $R^{3'}$ of the formula (Va') is a phenyl group substituted with a halogenoalkoxy group.

30. The compound according to claim 24, in which $R^{3'}$ of the formula (Va') is 4-(2,2,3,3-tetrafluoropropoxy)phenyl or 4-(1,1,2,2-tetrafluoroethoxy)phenyl.

31. A method of preparing a compound of the formula (Va') of claim 24:

which comprises reducing a compound of the formula (Va):

(Va)

wherein the symbols have the same meanings as defined above.

32. The compound according to claim 1, wherein R is a methine group having a functional group of R is selected from the group consisting of a silyl group, a double bond, and an optionally activated hydroxyl group.

* * * * *